United States Patent
Dvries Arturo et al.

(10) Patent No.: US 12,351,592 B2
(45) Date of Patent: Jul. 8, 2025

(54) METFORMIN COMPLEXES WITH TRANSITION METALS AND P GROUP ELEMENTS

(71) Applicant: UNIVERSIDAD SANTIAGO DE CALI, Cali (CO)

(72) Inventors: Richard Fernando Dvries Arturo, Cali (CO); Octavio Piñeros, Cali (CO); Stephanny Villamizar Delgado, Cali (CO)

(73) Assignee: UNIVERSIDAD SANTIAGO DE CALI, Cali (CO)

( * ) Notice: Subject to any disclaimer, the term of this patent is extended or adjusted under 35 U.S.C. 154(b) by 601 days.

(21) Appl. No.: 17/610,031

(22) PCT Filed: Aug. 7, 2020

(86) PCT No.: PCT/IB2020/057476
§ 371 (c)(1),
(2) Date: Nov. 9, 2021

(87) PCT Pub. No.: WO2021/024231
PCT Pub. Date: Feb. 11, 2021

(65) Prior Publication Data
US 2022/0315608 A1    Oct. 6, 2022

Related U.S. Application Data

(60) Provisional application No. 62/884,597, filed on Aug. 8, 2019.

(51) Int. Cl.
| | |
|---|---|
| *C07F 1/08* | (2006.01) |
| *C07F 3/06* | (2006.01) |
| *C07F 9/94* | (2006.01) |
| *C07F 15/02* | (2006.01) |
| *C07F 15/04* | (2006.01) |
| *C07F 15/06* | (2006.01) |

(52) U.S. Cl.
CPC .................. *C07F 1/08* (2013.01); *C07F 3/06* (2013.01); *C07F 9/94* (2013.01); *C07F 15/02* (2013.01); *C07F 15/04* (2013.01); *C07F 15/06* (2013.01); *C07B 2200/13* (2013.01)

(58) Field of Classification Search
CPC ...... C07F 1/08; C07F 3/06; C07F 9/94; C07F 15/02; C07F 15/04; C07F 15/06; C07B 2200/13; A61K 31/555; C07C 279/26; A61P 3/10
See application file for complete search history.

(56) References Cited

PUBLICATIONS

Al-Saif et al. "Synthesis, spectroscopic, and thermal investigation of transition and non-transition complexes of metformin as potential insulin-mimetic agents" Journal of Thermal Analysis and Calorimetry, 2012, vol. 111, pp. 2079-2096.*
CAS Registry No. 1141269-16-0 (Year: 2009).*
Olar et al. Copper (II) Complexes with N,N-dimethylbiguanide thermal, spectroscopic and biological characterization (Journal of Thermal Analysis and Calorimetry, vol. 92, 1, 239-243). (Year: 2008).*
Lemoine et al. Crystal structure of bis(N, N-dimethylbiguanide)nickel(II) salicylate (Z. Kristallogr. NCS 214, 369-370). (Year: 1999).*
Al-Saif et al. Synthesis, spectroscopic, and thermal investigation of transition and non-transition complexes of metformin as potential insulin-mimetic agents (J Therm Anal Calorim, 111:2079-2096). (Year: 2013).*
Brock et al. A Rare Example of Square Planar Zinc (Inorg. Chem. 33, 2491-2492). (Year: 1994).*
Krishan et al. Synthesis, spectral, mass and X-ray diffraction studys of Cu and Zn complexes with Metformin—an oral antidiabetic allopathic drug (J. Indian Chem. Soc., 91, 367-372). (Year: 2014).*

* cited by examiner

*Primary Examiner* — Joseph K McKane
*Assistant Examiner* — Meghan C Heasley
(74) *Attorney, Agent, or Firm* — Dinsmore & Shohl LLP

(57) ABSTRACT

Disclosed herein is an invention that refers to hydrochloride metformin complexes with transition metals and group P elements, such as cobalt (II), nickel (II), copper (II), zinc (III), iron (II), bismuth (III) and their preparation method. Additionally, the present invention offers crystalline forms of the metformin-cobalt (II) complex, metformin-nickel complex and metformin-copper complex as well as methods for therapeutic use in patient treatment and their preparation method.

4 Claims, 23 Drawing Sheets

METFORMIN COMPLEXES WITH TRANSITION METALS AND P GROUP ELEMENTS

RELATED APPLICATIONS

The present application is a U.S. National Phase of PCT/IB2020/057476, entitled "METFORMIN COMPLEXES WITH TRANSITION METALS AND P GROUP ELEMENTS" and filed Aug. 7, 2020, which claims priority to U.S. provisional application No. 62/884,597 entitled "Metformin complexes with transition metals and P group elements, methods for therapeutic use and preparation method" and filed Aug. 8, 2019, the entire contents of both are hereby incorporated in their respective entireties.

The present invention relates to the technical field of metformin complexes with transition metals and elements of group P, to the methods for therapeutic use in the treatment of patients with overweight and obesity, and to the preparation method.

BACKGROUND ART

About 100 million people all over the world have type II diabetes (NIDDM), that is characterized by hyperglycemia due to the excessive production of liver glucose and resistance to peripheral insulin, from which the root causes are still unknown. Hyperglycemia is considered the leading risk factor for the development of diabetic complications.

This disease is linked to metabolic syndrome, cardiovascular, and renal problems that increase the morbidity and mortality of people suffering from it. Obesity is also linked to an increase in the incidence and prevalence of type II diabetes and some types of cancer. The incidence of diabetes is on the rise and affects between 8% and 12% of the obese population over 40 years old.

Obesity is the most critical epidemic of the $21^{st}$ century since it is related to other pathologies such as cardiovascular disease, cancer, and type II diabetes, which consume massive resources of state-owned and family finances.

Anti-obesity pharmaceuticals have developed drugs which include different action mechanisms acting on the central nervous system such as appetite reduction, altering the metabolism, or inhibiting caloric absorption. These commercial drugs have revealed severe adverse effects that have forced their market recall. For instance, Sibutramine and Rimonabant, whose action mechanism affects the central nervous system regarding serotoninergic, adrenergic and dopaminergic pathways, in the states of satiety hunger, appetite, and anorexia, were withdrawn from the market. Other medications act on a peripheral level such as Orlistat, yet they have been reported to exhibit severe adverse effects such as diarrhea and abdominal pains.

Currently, one of the most commonly used pharmaceutical alternatives is the hydrochloride metformin commercial formula, which is widely sought due to its effectiveness and safeness. This drug is mostly aimed at the population with type II diabetes. However, it has proven to help in the treatment of obesity, cancer, and infectious diseases related to protozoans (Malaria) and bacteria (TBC), among others.

On a different matter, transition metals such as cobalt, nickel, and copper among others, are considered biometals, since they are immersed in many biochemical processes essential for the operation of biomolecules involved in energy production, hematopoietic metabolic processes, and neural operation. Based on transition metals, different metallic complexes have been obtained, which exhibit activity for the treatment of metabolic diseases and type II diabetes.

Currently, there are no solutions focused on the development of new pharmaceuticals that intervene in the intestine-brain axis and the operation of the gastroenteropancreatic system, specifically defining the hypothalamus as the homeostatic center of the appetite status and, hence, control body weight. Additionally, some secondary uses of older substances have not been assessed in the pharmaceutical industry, based on monotherapies or possible combinations with indications for obesity management. These new pharmaceuticals and their derivatives must have a peripheral action mechanism and present minimum adverse effects.

Considering this problem and a lack of pharmaceutical options, this work focuses on the development of new complexes based on metformin, transition metals and elements of the group P, to propose new therapeutic alternatives, by taking advantage of the characteristics of current drugs in synergy with the activity of metallic cations.

SUMMARY OF THE INVENTION

The present invention relates to new metformin complexes with transition metals as iron (II), cobalt (II), nickel (II), copper (II) and Zinc (II), and elements of group P such as bismuth (III).

Further, the invention relates to methods for therapeutic use of the above defined metformin-transition metal complexes and to the preparation method thereof.

The new compounds of the invention, by having a therapeutic effect on a cellular level, specifically in the mitochondria, attack the energetic core of the organism leading to higher efficiency in weight reduction in contrast with the technologies that have an impact in the central nervous system. This translates into lower action times and lesser secondary effects.

The present invention seeks to provide a solution to this problem(s) by generating complexes from metformin that are useful for the treatment of diabetes, particularly type II diabetes, as well as hyperglycemia, obesity, hypertriglyceridemia, diabetic complications, atherosclerosis, cancer, and related diseases.

Particularly, the present invention offers new crystalline forms of the metformin complexes of the invention as defined above.

Accordingly, the present invention also relates to the crystalline forms of metformin-transition complexes as defined above, preferably to the crystalline forms of complex metformin-iron (II), metformin-cobalt (II), metformin-nickel (II), metformin-copper (II), metformin-Zinc (II) and metformin-bismuth (III), and more preferably to the crystalline forms of complex metformin-cobalt (II) and metformin-nickel(II).

Present invention also relates to the preparation method of the above defined crystalline forms of metformin complexes.

Metformin is comprised of two molecules of guanidine, a colorless alkaline compound. Its chemical structure consists of primary, secondary and tertiary amines scaffold, giving rise to highly polar compounds, also considered as Lewis bases. Hydrochloride metformin is represented by the following structural formula depicted in formula I:

Formula 1

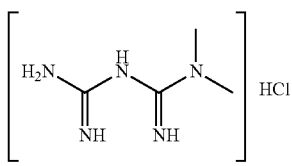

According to some embodiments of the invention, the metformin-transition metals complexes obtained can be planar square, tetrahedral or octahedral form depending on the metal center used.

Accordingly, a first aspect of the invention relates to a metformin-transition metal complex of any of the following formulas (a), (b), (c) or (d):

(a)

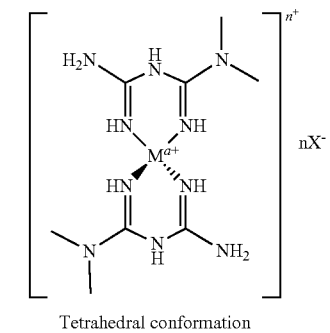

Tetrahedral conformation (b)

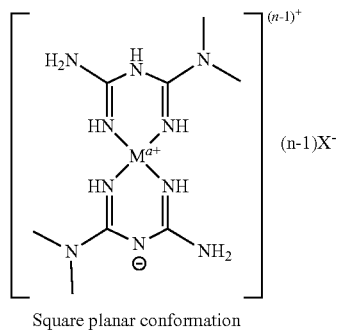

Octahedral conformation (c)

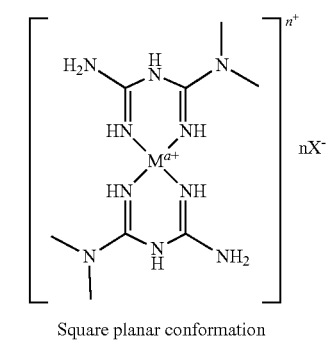

Square planar conformation (d)

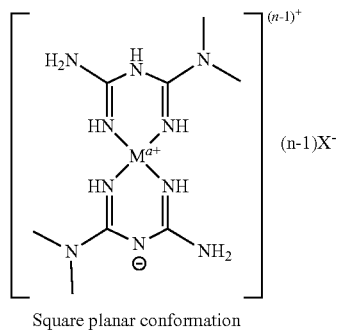

Square planar conformation wherein $M^{n+}$ (n+=positive charge) corresponds to metals with tetrahedral or square planar conformations for nickel (II), copper (II) and zinc (III) (formula (a), formula (c) or formula (d)) or octahedral conformations for cobalt (II), copper (II), iron (II) and bismuth (III) (formula (b)).

In another embodiment the invention relates to the metformin-transition metal complexes as defined above, selected from metformin-copper complex, metformin-iron complex, metformin-bismuth complex, metformin-nickel complex, metformin-zinc complex.

Another aspect of the present invention relates to the crystalline form of the metformin-transition metal complexes.

In another embodiment, the invention relates to a crystalline form of metformin-cobalt complexes characterized by powder X-ray diffraction that comprises the following 2Θ values: 9.82; 10.31; 10.59; 10.67; 11.62; 12.12; 12.66; 13.04; 14.11; 14.53; 15.07; 15.39; 15.57; 16.06; 16.24; 16.59; 17.11; 17.47; 17.99; 18.47; 19.12; 19.71; 20.05; 20.72; 20.99; 21.28; 21.46; 21.69; 22.08; 22.94; 23.16; 23.31; 23.67; 24.03; 24.50; 25.21; 25.51; 25.87; 26.25; 26.87; 27.19; 27.47; 27.87; 28.09; 28.39; 28.64; 28.86; 29.48; 30.11; 30.41; 31.03; 31.31; 31.68; 32.19; 32.37; 32.53; 32.74; 33.20; 33.52; 33.99; 34.44; 34.63; 35.02; 35.23; 35.85; 36.16; 36.66; 37.17; 37.81; 38.07; 38.49; 38.72; 38.95; 39.24; 39.48; 39.70; 39.90; 40.03; 40.14; 40.38; 40.87; 41.36; 41.66; 42.21; 42.37; 42.59; 42.80; 43.16; 43.35; 44.00; 44.19; 44.41; 44.79; 45.11; 45.38; 45.55; 45.79; 46.06; 46.63; 47.37; 48.05; 48.45; 48.67; 49.00; 49.35; 49.81.

In another embodiment, the invention relates to a crystalline form of metformin-Nickel complexes characterized by powder X-ray diffraction that comprises the following 2Θ values: 9.78; 11.62; 14.24; 15.60; 16.86; 19.13; 20.14; 20.85; 23.25; 23.34; 23.64; 23.97; 24.68; 25.80; 26.33; 26.71; 27.53; 28.85; 30.83; 31.36; 31.96; 32.69; 33.61; 34.09; 34.45; 34.82; 34.99; 35.44; 35.76; 36.14; 36.44; 36.75; 37.17; 37.75; 37.98; 38.32; 38.46; 38.66; 38.83; 39.44; 39.76; 40.32; 40.90; 41.36; 41.74; 41.84; 41.96; 42.08; 42.30; 42.44; 42.79; 43.19; 43.65; 44.15; 44.53; 44.83; 45.31; 45.64; 45.83; 46.11; 46.39; 46.53; 46.97; 47.52; 47.74; 48.06; 48.26; 48.47; 48.76; 49.04; 49.47; 49.62.

In another embodiment, the invention relates to a crystalline form of metformin-Copper complexes characterized by powder X-ray diffraction that comprises the following 2Θ values: 9.65; 11.78; 14.05; 15.31; 16.42; 18.79; 18.90; 19.37; 20.31; 21.40; 23.15; 23.49; 23.82; 24.33; 24.80; 24.92; 25.25; 26.03; 26.82; 28.22; 29.07; 29.22; 30.33; 30.68; 31.48; 31.81; 32.00; 32.08; 33.02; 33.19; 33.61; 33.94; 34.59; 35.73; 36.04; 36.42; 36.72; 36.89; 37.07;

37.95; 38.21; 38.33; 38.58; 38.91; 39.19; 39.39; 40.54; 40.64; 40.80; 40.95; 41.30; 41.57; 41.79; 42.39; 42.86; 43.05; 43.23; 43.41; 43.59; 44.10; 44.23; 44.78; 45.10; 45.27; 45.86; 46.07; 46.94; 47.14; 47.33; 47.54; 48.02; 48.20; 48.45; 48.63; 48.84; 49.12; 49.52; 49.72.

In another embodiment, the invention relates to a crystalline form of metformin-zinc complexes characterized by powder X-ray diffraction that comprises the following 2⊖ values: 7.68; 13.71; 14.07; 14.41; 14.79; 15.39; 16.25; 17.26; 18.11; 18.49; 18.94; 19.20; 19.42; 22.04; 22.88; 23.66; 24.44; 24.82; 25.12; 25.24; 26.89; 27.45; 27.71; 28.00; 28.35; 28.63; 28.93; 29.06; 29.58; 29.73; 30.14; 30.65; 30.88; 31.06; 31.30; 31.48; 32.16; 32.71; 33.36; 33.75; 34.11; 34.93; 35.69; 36.85; 37.15; 37.46; 37.68; 37.85; 38.11; 38.39; 38.53; 38.79; 38.97; 39.11; 39.44; 39.74; 40.30; 40.40; 40.71; 40.85; 41.61; 42.08; 42.17; 42.58; 42.79; 43.11; 43.41; 43.74; 44.22; 44.54; 44.85; 44.94; 45.20; 45.48; 45.60; 45.85; 46.22; 46.46; 46.63; 47.08; 47.28; 47.36; 47.58; 48.23; 48.42; 48.73; 48.99; 49.12; 49.48; 49.44.

According to another aspect related to the invention, metformin can form coordination compounds using two options: 1) by de-protonating the amine nitrogen with the help of a strong base, thus generating a negatively charged molecule, i.e., a nucleophile that can be coordinated to a central metallic species; 2) a base is added that allows the formation of a neutral metformin, which can act as a Lewis base through free pairs of amines to build complexes with the metallic cations $Fe^{2+}$, $Zn^{2+}$, $Ni^{2+}$, $Cu^{2+}$, $Co^{2+}$, and $Bi^{3+}$. In this second option, the metallic centers will behave as Lewis acids, i.e., electrophiles, leading to new metallic coordination complexes or biologically active metallodrugs.

According to the reactivity of the ligand, the possible general formulas that can be obtained are $[M^{n+}(Mfn)_n]\cdot nX^-$, $[M^{n+}(Mfn)_{n+1}]\cdot nX^-$, $[M^{n+}(Mfn)^{m-}_n]\cdot n\text{–}mX$, wherein:

M represents central cation ($Fe^{2+}$, $Zn^{2+}$, $Ni^{2+}$, $Cu^{2+}$, $Co^{2+}$, and $Bi^{3+}$);

n represents positive charge;

m represents negative charge;

X represents any monoanion; and

Mfn represents the metformin.

According to another aspect of the invention, a preparation method has been developed for metformin-transition metal complexes, spectroscopic, thermal, and structural characterization.

According to another aspect, the invention relates to a preparation procedure for a crystalline form of the metformin-cobalt complex that comprises any of the subsequent stages 1) or 2):

1) Mixing 4 mL of an aqueous solution of the metformin (Mfn) ligand ($C_4H_{12}N_5Cl$) (510 mg, 3.08 mmol) with 4 mL of the aqueous solution of cobalt (II) chloride ($CoCl_2\cdot 6H_2O$) (200 mg, 1.54 mmol), add 5 mL of NaOH 2 $molL^{-1}$, take to reflux and shake for 60 minutes. Cool off and filter to obtain a crystalline form of the metformin-cobalt complex; or 2) Mixing methanolic solutions of 10 mL of the ligand Mfn ($C_4H_{12}N_5Cl$) (33 mg, 0.2 mmol) with 1.2 equivalents of NaOH and 5 mL of the cobalt (II) chloride salt ($CoCl_2\cdot 6H_2O$) (23 mg, 0.1 mmol), take to reflux and shake for 60 minutes at 100° C. Cool off at room temperature to obtain the crystalline form of the metformin-cobalt complex.

According to another aspect, the invention relates to a preparation procedure of a crystalline form of the metformin-nickel complex that comprises any of the subsequent stages 1) or 2):

1) Mixing 4 mL of the aqueous solution of the ligand, Mfn ($C_4H_{12}N_5Cl$) (510 mg, 3.08 mmol) with 4 mL of the aqueous solution of nickel sulfate ($NiSO_4\cdot 6H2O$) (200 mg, 1.54 mmol) into 4 mL of KOH 2 $molL^{-1}$, take to reflux and shake for 60 minutes. Cool off and filter to obtain a crystalline form of the metformin-nickel complex; or 2) Dissolve (66 mg, 0.4 mmol) of the ligand, Mfn ($C_4H_{12}N_5Cl$), into 4 mL of aqueous solution of nickel sulfate ($NiSO_4\cdot 6H2O$) (47 mg, 0.2 mmol), add (53 mg, 1.33 mmol) de NaOH and shake with the help of a magnet for 60 minutes, to obtain the crystalline form of the metformin-nickel complex According to another aspect, the invention relates to a preparation procedure of a crystalline form of the metformin-zinc complex that comprises any of the subsequent stages 1) or 2):

1) In a flat-bottomed flask, 4 mL of an aqueous solution of the Mfn ligand ($C_4H_{12}N_5Cl$) (119 mg, 0.72 mmol) were mixed with 4 mL of an aqueous solution of zinc (II) chloride ($ZnCl_2$) (200 mg, 1.46 mmol) and 1.2 equivalents of NaOH. The reaction mixture was stirred for 2.5 hours at room temperature. The resulting solution was filtered to obtain a colorless solid; or 2) In a flat bottom flask, (66 mg, 0.4 mmol) of the ligand, Mfn ($C_4H_{12}N_5Cl$) are dissolved in 4 mL of an aqueous solution of nickel sulfate ($NiSO_4\cdot 6H_2O$) (47 mg, 0.2 mmol) to which (53 mg, 1.33 mmol) of NaOH is added. It was magnetically stirred for 60 minutes. The resulting precipitate was filtered and washed with water (orange solid).

According to another aspect, the invention relates to a preparation procedure of a crystalline form of the metformin-copper complex that comprises the subsequent stages: In a flat-bottomed flask, 4 mL of an aqueous solution of the Mfn ligand ($C_4H_{12}N_5Cl$) (33 mg, 0.2 mmol) were mixed with 4 mL of an aqueous solution of copper (II) chloride ($CuCl_2\cdot 2H_2O$) (200 mg, 1.17 mmol) and 1.2 equivalents of NaOH. The reaction mixture was stirred for 60 minutes at room temperature. The resulting solution was concentrated, cooled to room temperature, and filtered to obtain a purple solid.

According to another aspect, the invention relates to a preparation procedure of a crystalline form of the metformin-iron complex that comprises the subsequent stages: In a flat-bottomed flask, 4 mL of an aqueous solution of the Mfn ligand ($C_4H_{12}N_5Cl$) (33 mg, 0.2 mmol) were mixed with 4 mL of an aqueous solution of iron (II) chloride ($FeCl_2\cdot 6H_2O$) (200 mg, 0.74 mmol) and 1.2 equivalents of NaOH. The reaction mixture was stirred for 60 minutes at room temperature. The resulting solution was concentrated, cooled to room temperature, and filtered to obtain a deep red solid.

According to another aspect, the invention relates to a preparation procedure of a crystalline form of the metformin-bismuth complex that comprises the subsequent stages: In a flat bottom flask, 4 mL of the aqueous solution of the ligand Mfn ($C_4H_{12}N_5Cl$) (204 mg, 1.23 mmol) were mixed with 4 mL of the methanol-based solution of bismuth (III) nitrate (200 mg, 0.41 mmol) to which 1.2 equivalents of NaOH were added. It was taken to reflux for 60 minutes. After it cooled off, it was filtered by separating the obtained solid (cream color solid).

In one particular aspect of the invention, the same methodology was followed for the synthesis of all coordination compounds. However, in some cases, the bases such as NaOH, KOH, and triethylamine were varied to determine the effect of a strong base and a weak base. Furthermore, tests were carried out with different solvents in order to find the best reaction and crystallization environment.

The metformin complexes can be in the form of salt; additionally, according to the present invention, a method is proposed to treat hyperglycemia, including Type II diabetes (DMNDI) and/or Type I diabetes (DMDI) in which a therapeutically effective dose of the metformin-hydrochloride complex is given to the patient, including its crystalline and salt-based forms.

Metformin-transition metal complexes can show other polymorphic shapes.

In another embodiment, the obtained metformin-metal complexes of Co(II), Ni(II) and Cu(II) were cell viability evaluated in C2C12 (ATCCCRL-1772TM) mouse muscle cells and HepG2 (ATCC HB-8065TM) human liver carcinoma cells by the MTT assay after the treatment of the three different compounds for 4 hours (C2C12) or 48 hours (HepG2), to determine the potential of the compounds as new safe drugs. The results demonstrate that the compounds exhibit low cytotoxicity at doses less than 250 µg/ml with a cell viability greater than 80%.

The formulations of the present invention are included for oral, nasal, topical, buccal, sublingual, rectal, vaginal and/or parenteral administration. The formulations can be presented in the unit or multiple dosage form, immediate, delayed or prolonged release and can be prepared by any method known in the pharmacy art. The amount of active ingredient that can be combined with carrier materials or excipients to produce a single dosage form will be the amount of the compound that produces a therapeutic effect. In general, this amount will range, for solid dosage forms, between about 50 mg to 800 mg to be administered every 8 hours in immediate release forms, 150 mg to 1200 mg for 12 hour prolonged release forms, or 150 to 2400 mg for sustained release forms in 24 hours. For non-solid dosage forms, concentrations between 1% and approximately 99% of the active ingredient, preferably between approximately 5 percent and approximately 70 percent.

Another aspect of the invention relates to a pharmaceutical composition which comprises the metformin-metal complexes as defined above.

The pharmaceutical forms for the oral administration of formulations of the invention may be capsules, sachets, pills, tablets, lozenges (using a flavored base, usually sucrose and gum arabic or tragacanthin), powders, granules, or as a liquid solution or suspension, aqueous or non-aqueous, or as a liquid emulsion of oil in water (o/w) or water in oil (w/o), as an elixir or syrup, or as a tablet (using an inert base, such as gelatin and glycerin, or sucrose). Each contains a predetermined amount of a metformin complex of the present invention as a drug or active ingredient.

Other pharmaceutical forms of the invention are those of prolonged release to facilitate administration and adherence. This can be done in tablets and capsules, using the drugs described and approved in pharmacopeias. These new complexes have the characteristic of having a neutral polarity in most cases, which gives them a greater permeability to improve its oil/water partition coefficient, increasing its absorption, decreasing the amount of the active ingredient to be used to achieve a therapeutic effect. Afterward, the process will continue to determine its permeability and solubility according to the pharmacopeia, subsequently pharmacokinetics in vitro and animals. Pharmacodynamic tests in mitochondrial and hepatic models.

While the present invention has been described in terms of particular embodiments and applications, in both summarized and detailed forms, it is not intended that these descriptions limit in any way its scope to any such embodiments and applications, and it will be understood that many substitutions, changes, and variations in the described embodiments, applications and details of the method and system illustrated herein and of their operation can be made by those skilled in the art without departing from the spirit of this invention.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. The expressions "consisting" and/or "consisting essentially of" are used instead of comprising as a synonym expression.

Unless otherwise defined, all terms (including technical and scientific terms) used herein have the same meaning as commonly understood by one having ordinary skill in the art this invention belongs to. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In the description of the invention, it will be understood that a number of techniques and steps are disclosed. Each of these has an individual benefit, and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims in a non-provisional patent, a PCT application or further patent application referred to claiming priority to this Provisional Patent Application should be read with the understanding that such combinations are entirely within the scope of the invention and the claims.

New metformin complexes with transition metals and P group elements, methods for therapeutic use and their preparation method, are discussed herein. In the following description, for explanation purposes, numerous specific details are set forth in order to provide a thorough understanding of the present invention. It will be evident, however, to someone skilled in the art that the present invention may be practiced without these specific details.

The present disclosure is to be considered as an exemplification of the invention and is not intended to limit the invention to the specific embodiments illustrated by the figures or description below.

Another aspect of the present invention relates to the metformin-transition metal complex as defined above or to a pharmaceutical composition thereof, for use in therapy.

Hydrochloride metformin is widely used in the treatment and prevention of type II diabetes, especially with patients suffering from overweight and normal renal function. Its advantage is that it does not produce hypoglycemic crises that can be life-threatening. It also helps to reduce LDL levels and blood triglyceride and is the only medication known to prevent cardiovascular diseases linked to diabetes.

It was initially used to treat malaria and as an anti-bacterial anti-viral drug. Metformin has a bioavailability between 40 and 60% and is not bound to plasmatic proteins. It is not metabolized by the liver and is excreted in an unaltered form by the kidney.

Its tissue distribution is speedy, accumulating in the digestive tube and in lower proportions in the liver and the kidney. It has slow access to erythrocytes (5% of the blood dose), reaching a lower concentration in blood than in plasma. The distribution volume (Vd) is 654±358 I.

Its pharmacodynamics focus on controlling the glycogenesis in the liver, increasing the cellular intake of glucose and reducing appetite, as well as the synthesis of fatty acids and triglycerides, without producing hyperinsulinemia. It is the only glucose-lowering molecule that reduces the risk of macro-vascular and micro-vascular disorders and shields the body against cardiovascular complications linked to diabetes.

Metformin is a safe and effective drug, tested over the course of many years and in millions of patients. It has seldom shown side effects, which include lactic acidosis, which is tied to an altered renal function.

On a different matter, elements of block P (that have their valence electrons in the p orbital) are located in the III-A VIII-A groups of the periodic table of elements. In these elements, the outmost energetic level corresponds to p orbitals. Transition metals, also known as transition elements, is the group where cobalt belongs to. Cobalt has some characteristics of transition metals, which include the electronic setting of orbital d, partially full of electrons. This has implications in the structure and the mitochondrial respiratory chain, which is based on the transportation of electrons.

It exhibits low oxidation states since the compounds in which cobalt has an oxidation status of +4 are uncommon. The oxidation status +2 is highly frequent, as well as +3. There are also essential complexes with an oxidation status of +1.

Cobalt is essential for all animals, including humans. It is part of the cobalamin (B12 Vitamin). A cobalt deficiency can lead to anemia. Nonetheless, secondary anemia due to cobalt deficiency is quite rare since consuming traces of the element is enough to maintain proper homeostasis. Furthermore, cobalt is an element that can be found in various foods, which makes it hard to suffer a deficiency due to low intake.

Proteins based on cobalamin use the corrin ring to keep the cobalt together. Coenzyme B12 offers the C—Co link, which participates in the reactions. However, in the case of high concentrations of these metallic ions, severe health consequences can arise. Ranges are yet to be defined for their use in humans with therapeutic and nutritional purposes.

Accordingly, another aspect of the invention relates to a method to treat a disease in which the patient is given a therapeutically effective dose of a metformin-transition metal complex or a pharmaceutically acceptable salt thereof.

A further aspect of the invention relates a method to treat a disease illnesses in which the patient is given a therapeutically effective dose of a metformin-transition metal complex or a pharmaceutically acceptable salt thereof, in which the disease is selected from diabetes, specially type II diabetes, as well as hyperglycemia, obesity, hypertriglyceridemia, diabetic complications, atherosclerosis, cancer and related illnesses, preferably wherein the disease is selected from diabetes, obesity, hypertriglyceridemia, hyperglycemia, atherosclerosis and cancer, and more preferably wherein the disease is selected from type II diabetes (DMNDI), type I diabetes (DMDI), obesity, metabolic syndrome, hypertriglyceridemia, hyperglycemia, atherosclerosis, malaria and cancer.

Another aspect of the invention relates to a method to treat a disease selected from diabetes, obesity, hypertriglyceridemia, diabetic complications, atherosclerosis, cancer and related illnesses in which the patient is given a therapeutically effective dose of a metformin-transition metal complex or a pharmaceutically acceptable salt thereof, preferably wherein the disease is selected from diabetes, obesity, hypertriglyceridemia, hyperglycemia, atherosclerosis and cancer, and more preferably wherein the disease is selected from type II diabetes (DMNDI), type I diabetes (DMDI), obesity, metabolic syndrome, hypertriglyceridemia, hyperglycemia, atherosclerosis, malaria and cancer or the patience experience protozoal infection.

EXAMPLES

Figure 1:
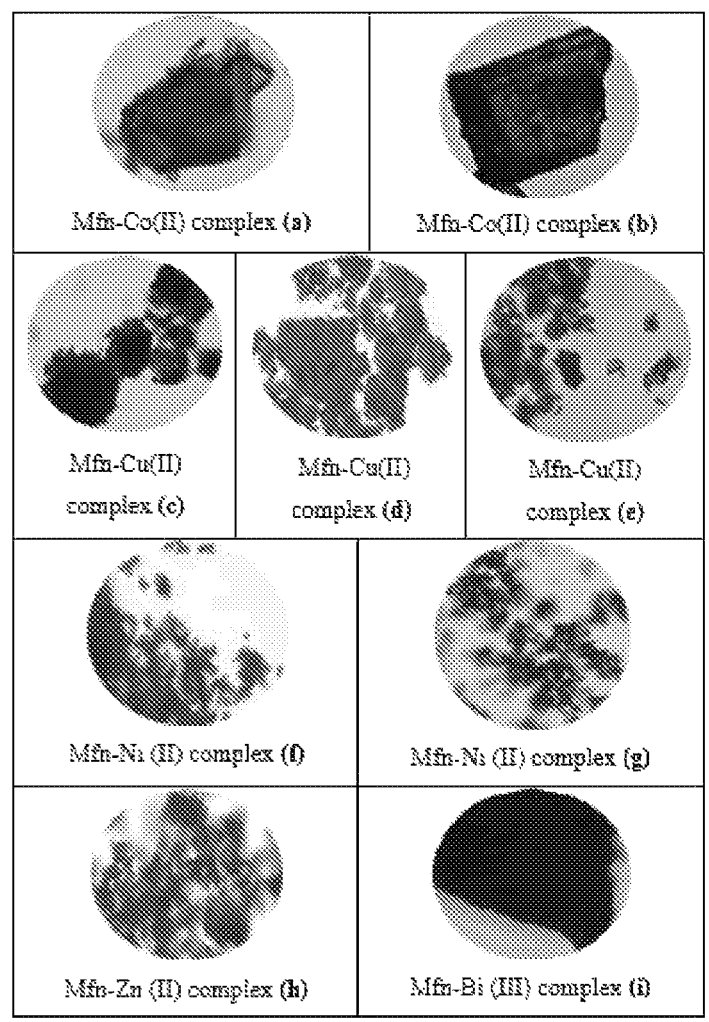
FIG. 1. Illustrates photographs of the nine complexes of metformin-metal of the present invention.
Figure 2:
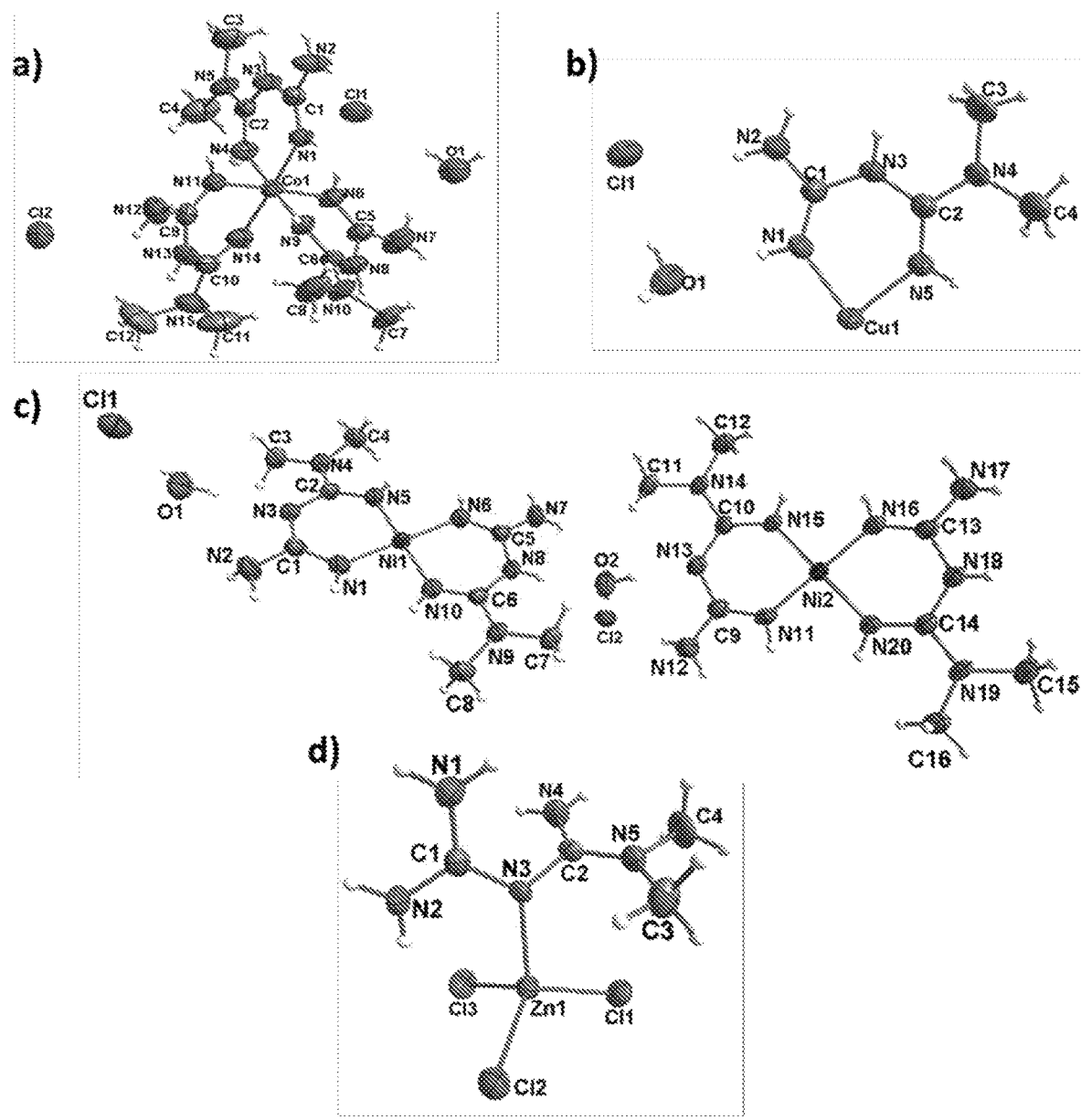
FIG. 2. Illustrates the structures of the obtained compounds a) $[Co(C_4H_{12}N_5)_3]Cl_2 \cdot nH_2O$, b) $[Cu(C_4H_{12}N_5)_2]Cl_2 \cdot H_2O$, c) $[Ni(C_4H_{11}N_5)_2]Cl \cdot H_2O$ and d) $[Zn(C_4H_{11}N_5)Cl_3]$ FIG. 3. Illustrates the powder X-ray diffraction pattern for the compound MfnCo (a).
Figure 3:
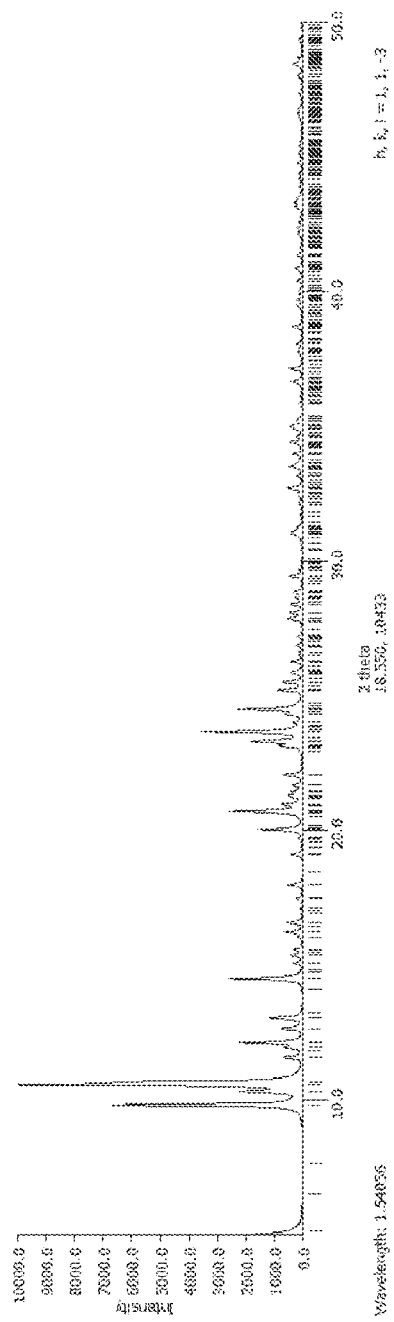
Figure 4:
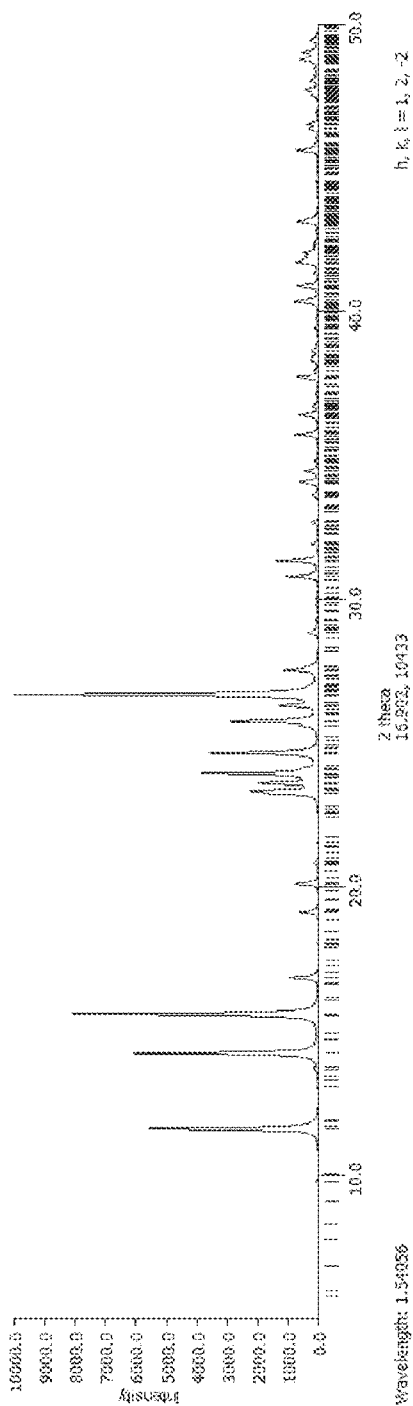
FIG. 4. Illustrates the powder X-ray diffraction pattern for the compound MfnNi (f).

Preparation Procedure of the Metformin-Transition Metals Complexes

The first procedure for the preparation of the hydrochloride-metformin-cobalt complex is now described:

In a flat-bottomed flask, 10 mL of methanolic solutions of the Mfn ligand ($C_4H_{12}N_5Cl$) (33 mg, 0.2 mmol) were mixed with 1.2 equivalents of NaOH and 5 mL of cobalt (II) chloride ($CoCl_2 \cdot 6H_2O$) (23 mg, 0.1 mmol). The reaction mixture was refluxed for 60 minutes. The resulting solution was concentrated and cooled to room temperature. Cubic reddish crystals were obtained by slow evaporation after 4 weeks (yield=61.57%). Elemental Anal. Calcd for [Co($C_4H_{11}N_5$)$_3$]$Cl_2 \cdot 2H_2O$ ($C12H_{37}N15O2Cl2Co$): C, 26.05; H, 6.74; N, 37.97. Found: C, 25.86; H, 6.02; N, 37.21.

A second procedure for the preparation of the metformin-cobalt complex is the following:

In a flat bottom flask, 10 mL of methanolic solutions the Metformin ligand ($C_4H_{12}N_5Cl$) (33 mg, 0.2 mmol) were mixed with 1.2 equivalents of NaOH and 5 mL of the cobalt (II) chloride salt (II) ($CoCl_2 \cdot 6H_2O$) (23 mg, 0.1 mmol). It was taken to reflux and stirred for 60 minutes at 100° C. The resulting solution was cooled at room temperature allowing its evaporation in an evaporator, leading to a reddish solid.

In one embodiment, the first procedure for the preparation of a metformin-nickel complex is now described:

In a flat-bottomed flask, 4 mL of a solution of the Mfn ligand ($C_4H_{12}N_5Cl$) (66 mg 0.4 mmol) were mixed with 4 mL of aqueous nickel (II) sulfate solution ($NiSO_4 \cdot 6H_2O$) (47 mg, 0.2 mmol) and 53 mg of NaOH (1.3 mmol). The reaction mixture was stirred for 60 minutes at room temperature. The resulting solution was cooled to room temperature and filtered to separate the orange solid (crystalline powder) obtained. The obtained solid was dissolved in water, and HCl was added dropwise until dissolution. The compound was recrystallized by slow evaporation to obtain prism orange crystals (yield=53.70%). Elemental Anal. Calcd for [Ni($C_4H_{11}N_5$)($C_4H_{10}N_5$)]$Cl \cdot H_2O$ ($C8H_{23}N10OClNi$): C, 26.01; H, 6.27; N, 37.91. Found: C, 25.67; H, 5.81; N, 37.03.

In another embodiment, the second procedure for the preparation of a metformin-nickel complex is the following:

In a flat bottom flask, (66 mg, 0.4 mmol) of the ligand, Mfn ($C_4H_{12}N_5Cl$) are dissolved in 4 mL of an aqueous solution of nickel sulfate ($NiSO_4 \cdot 6H_2O$) (47 mg, 0.2 mmol) to which (53 mg, 1.33 mmols) of NaOH is added. It was magnetically stirred for 60 minutes. The resulting precipitate was filtered and washed with water (orange solid).

In another embodiment, the procedure for the preparation of a metformin-copper complex is the following:

In a flat-bottomed flask, 4 mL of an aqueous solution of the Mfn ligand ($C_4H_{12}N_5Cl$) (33 mg, 0.2 mmol) were mixed with 4 mL of an aqueous solution of copper (II) chloride ($CuCl_2 \cdot 2H_2O$) (200 mg, 1.17 mmol) and 1.2 equivalents of NaOH. The reaction mixture was stirred for 60 minutes at room temperature. The resulting solution was concentrated, cooled to room temperature, and filtered to obtain a purple solid. The solid was dissolved in water and recrystallized by slow evaporation to obtain purple needless crystals (yield=88.02%). Elemental Anal. Calcd for [Cu($C_4H_{11}N_5$)$_2$]$Cl_2 \cdot 2H_2O$ ($C8H26N10OCl2Cu$): C, 22.41; H, 6.11; N, 32.66. Found: C, 22.15; H, 6.21; N, 32.41.

In another embodiment, the procedure for the preparation of a metformin-iron complex is the following:

In a flat-bottomed flask, 4 mL of an aqueous solution of the Mfn ligand ($C_4H_{12}N_5Cl$) (33 mg, 0.2 mmol) were mixed with 4 mL of an aqueous solution of iron (II) chloride ($FeCl_2 \cdot 6H_2O$) (200 mg, 0.74 mmol) and 1.2 equivalents of NaOH. The reaction mixture was stirred for 60 minutes at room temperature. The resulting solution was concentrated, cooled to room temperature, and filtered to obtain a deep red solid.

In another embodiment, the procedure for the preparation of a metformin-bismuth complex is the following:

In a flat bottom flask, 4 mL of the aqueous solution of the ligand Mfn ($C_4H_{12}N_5Cl$) (204 mg, 1.23 mmols) were mixed with 4 mL of the methanol-based solution of bismuth (III) nitrate (200 mg, 0.41 mmols) to which 1.2 equivalents of NaOH were added. It was taken to reflux for 60 minutes. After it cooled off, it was filtered by separating the obtained solid (cream color solid).

Hence, the invention based on the synthesis of metal-metformin complexes (metal=$Fe^{2+}$, $Cu^{2+}$, $Co^{2+}$, $Zn^{2+}$, $Bi^{3+}$, $Ni^{2+}$) was carried out in one single step, through the use of reflux heating. According to the present invention, nine different compounds were obtained for which the physio-chemical properties were obtained, and analyzed through different spectroscopic, thermal and X-ray diffraction techniques, which are presented later on for each compound.

Furthermore, the reaction products were analyzed through optical microscopy, thus detecting crystals for compounds (a), (b), (e), (f) and (g), with irregular shapes of cubes, blocks, and plates.

TABLE 1

Physio-chemical properties of the obtained coordination compounds.

| Compound | Color | Texture | Solubility | Melting point (° C.) |
|---|---|---|---|---|
| MfnCo (a) | reddish orange | Solid | DMSO/MeOH/water (partially soluble) | 270 |
| MfnCo (b) | reddish orange | Solid | water/methanol | 246 |
| MfnCu (c) | pale Pink | Dusty | Insoluble | 245 |
| MfnCu (d) | fucsia Pink | cotton-like | DMSO | 225 |
| MfnCu (e) | Persian red | Dusty | Water | 255 |
| MfnNi (f) | Orange | Dusty | methanol (partially soluble) | 316 |
| MfnNi (g) | Orange | Dusty | DMSO/chloroform | 314 |
| MfnZn (h) | White | Dusty | DMSO | 229 |
| MfnBi (i) | White | Solid | — | |

The reported metformin-metal complexes were full characterized by single crystal X-ray diffraction, presenting the follow cell parameters and crystallographic information. Particularly, table 2 shows the crystallographic data of the metformin-metal complexes (M=Co, Ni, Cu and Zn) as shown:

TABLE 2

Crystallographic data and refinement parameters for
(1) $[Co(C_4H_{11}N_5)_3]Cl_2 \cdot 2H_2O$, (2) $[Ni(C_4H_{11}N_5)(C_4H_{10}N_5)]Cl \cdot H_2O$,
(3) $[Cu(C_4H_{11}N_5)_2]Cl_2 \cdot H_2O$ and (4) $[Zn(C_4H_{12}N_5)Cl_3]$ compounds.

| Compound | (1) | (2) | (3) | (4) |
|---|---|---|---|---|
| Emp. Formula | $C_{12}H_{33}N_{15}Co$, 2(Cl), $H_2O$ | $C_{16}H_{42}N_{20}Ni_2$, 2(Cl), $2H_2O$ | $C_8H_{22}N_{10}Cu$, 2(Cl), $2(H_2O)$ | $C_4H_{12}Cl_3N_5Zn$ |
| FW (g/mol) | 535.38 | 739.05 | 428.83 | 301.91 |
| Crystal system | | Monoclinic | | |
| Space Group | C2/c | $P2_1/c$ | $P2_1/n$ | $P2_1/c$ |
| Unit cell | | | | |
| a (Å) | 36.470 (2) | 13.3863 (6) | 5.1596 (14) | 12.5200 (12) |
| b (Å) | 8.5892 (6) | 7.4187 (5) | 11.562 (2) | 7.5140 (6) |
| c (Å) | 17.3656 (13) | 15.7512 (9) | 15.091 (4) | 13.0298 (13) |
| β (°) | 99.376 (6) | 104.757 (5) | 95.63 (3) | 113.199 (12) |
| Volume (Å$^3$) | 5367.1 (6) | 1512.64 (15) | 895.9 (4) | 1126.7 (2) |
| Z | 4 | 4 | 2 | 2 |
| ρ calcd (mg/m$^3$) | 1.325 | 1.618 | 1.590 | 1.780 |
| Abs. Coeff (mm$^{-1}$) | 0.872 | 1.476 | 1.541 | 2.856 |
| F(000) | 2248 | 772 | 446 | 608 |
| θ range (°) | 2.7-28.0 | 2.7-34.5 | 2.7-26.5 | 3.2-29.0 |
| Ref. collected/ Unique [R(int)] | 38196, 6485 [0.120] | 4364, 2843 [0.019] | 5415, 1863 [0.091] | 5154, 2966 [0.025] |
| Completeness (%) | 99.6 | 98.8 | 99.9 | 99.2 |
| Data/rest./param. | 6485/0/323 | 2843/0/111 | 1863/0/119 | 2966/0/120 |
| Gof on F$^2$ | 1.01 | 1.09 | 1.04 | 1.09 |
| R1 [I > 2σ(I)] | 0.0601 | 0.0512 | 0.0585 | 0.0373 |
| wR2 [I > 2σ(I)] | 0.1598 | 0.1314 | 0.1570 | 0.0928 |

The $[Co(C_4H_{11}N_5)_3]Cl_2 \cdot H_2O$ (MfnCo compound (b)) crystallizes within the monoclinic crystalline system with a space group C2/c. This compound is comprised of three molecules of ligand Mfn coordinated to the $Co^{2+}$ cation, two Cl anions and two molecules of crystallization water per asymmetric unit. The ligand is coordinated to the metallic cation through the nitrogen of the amino group forming a chelate. This coordination mode gives stability to the molecule and allows its formation. The cation is coordinated to six atoms of nitrogen, forming a compound with octahedral geometry. The new compound is an ionic compound where $[Co(C_4HN_{11}N_5)_3]^{2+}$ is the cation, and the chloride ions act as counter ions.

The $[Ni(C_4H_{11}N_5)_2]Cl \cdot H_2O$ (MfnNi compound (f)) compound was obtained as yellow crystals that crystallized in the C2/c monoclinic space group. The compound contains two cationic complexes, two chloride anions, and two water molecules in the asymmetric unit. The complexes are formed by one metformin ligand and one deprotonated metformin coordinated to the $Ni^{2+}$ center, forming a four-coordinated arrangement ($NiN_4$) with a distorted square planar polyhedron or parallelepiped.

The $[Cu(C_4H_{12}N_5)_2]Cl_2 \cdot H_2O$ (MfnCu compound (e)) was obtained as purple crystals. The asymmetric unit is formed by a half Cu' metallic cation located in a symmetry center, which is coordinated by one chelate metformin ligand, one chloride anion as a counter-ion, and one free water molecule. The complex is formed by the coordination of two chelate metformin ligands to generate a four-coordinated rectangular polyhedron ($CuN_4$).

The $[Zn(C_4H_{11}N_5)Cl_3]$ (MfnZn compound (h)) was obtained as colorless crystals with one $Zn^{2+}$ metal coordinated by three chloride anions and one protonated metformin molecule in the asymmetric unit. The final complex presents a tetrahedral ($ZnNCl_3$) arrangement around the Zn center.

Figure 5:
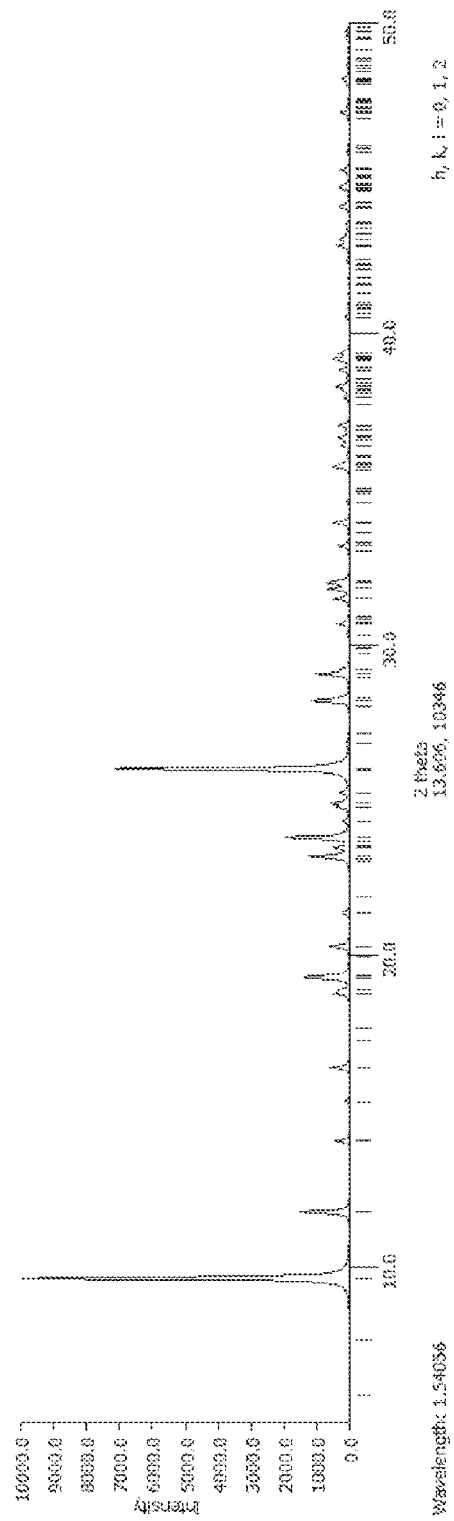
FIG. 5. Illustrates the powder X-ray diffraction pattern for the compound MfnCu (e).

FIG. 5 shows the infrared spectrum of the hydrochloride metformin ligand; the molecule is comprised by various types of bonds such as C—N, N—H, C—H, and C=N, corresponding to different functional groups that absorb radiation under specific wavelengths.

The characteristic bands of the functional groups in the spectrum: (C—N): 1053 cm$^{-1}$ and 1163 cm$^{-1}$; (C=N): 1562 cm$^{-1}$ and 1629 cm$^{-1}$; (C—H): 2811 cm$^{-1}$ and (N—H): 3168 cm$^{-1}$, 3293 cm$^{-1}$ and 3377 cm$^{-1}$. Additionally, a large intensity band is observed at 2358 cm$^{-1}$ that is due to the presence of $CO_2$ during the measuring process.

Figure 6:
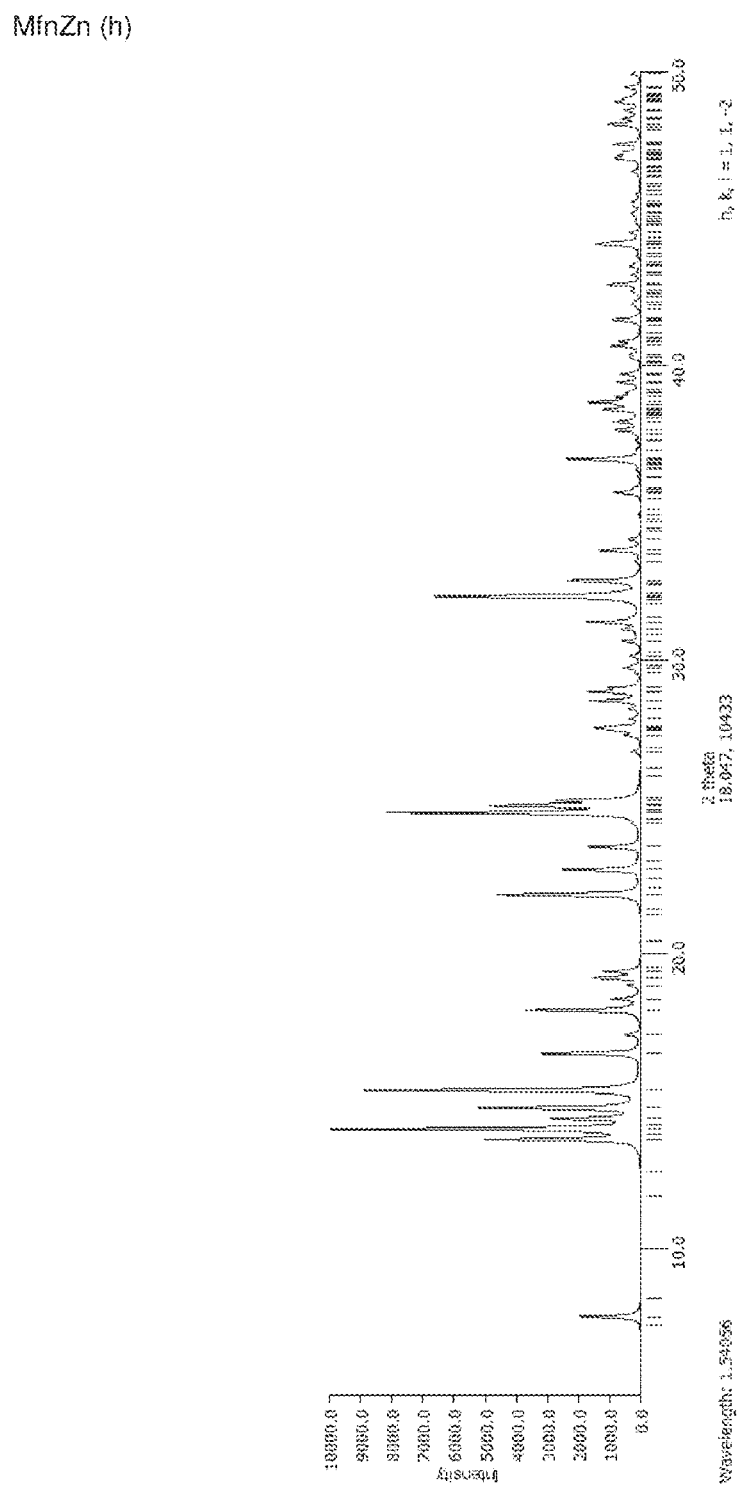
FIG. 6. Illustrates the powder X-ray diffraction pattern for the compound MfnZn (h).

FIG. 6 shows the obtained infrared spectrum for the metformin coordination compound of Co (II) (a) with the characteristic bands of the functional groups: (C—N): 1049 cm$^{-1}$ and 1226 cm$^{-1}$, where a slight displacement is evident under a higher wavelength in this last absorption band; (C=N): 1575 cm$^{-1}$; (C—H): 2859 cm$^{-1}$ and 2937 cm$^{-1}$. For the (N—H) group, a largely intense bandwidth is observed at 3336 cm$^{-1}$ and 3624 cm$^{-1}$. Finally, a band is present at 2358 cm$^{-1}$ due to the presence of $CO_2$ during the measuring process of the coordination compound.

Figure 7:
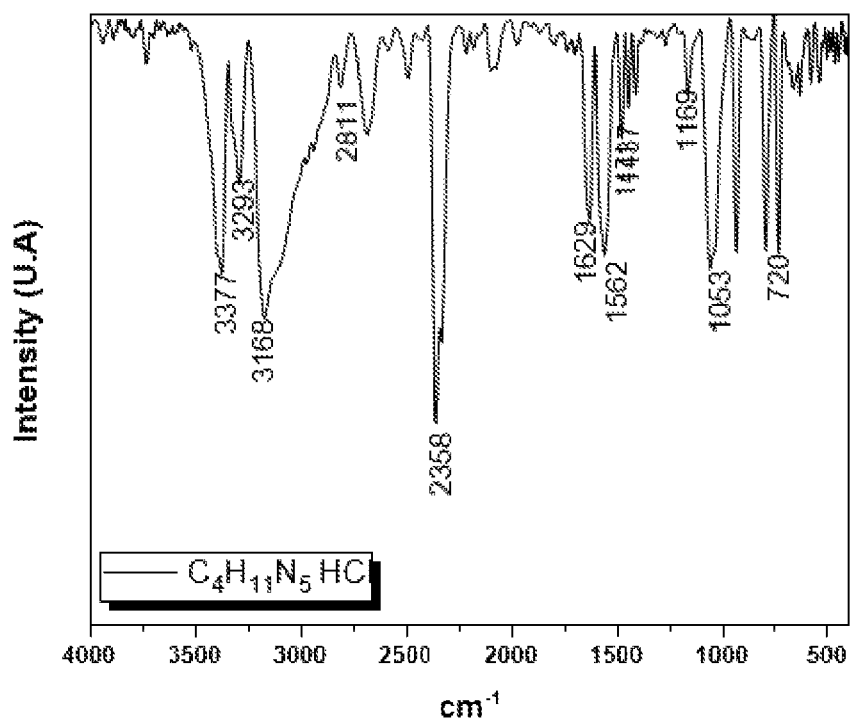
FIG. 7. Illustrates the Fourier transform infrared (FTIR) spectroscopic chart of metformin hydrochloride.

FIG. 7 shows the infrared spectrum for the cobalt coordination compound obtained for method 2, where the characteristic bands of the functional groups can be detailed: (C—N): 1062 cm$^{-1}$, 1192 cm$^{-1}$ and 1245 cm$^{-1}$, while a slight displacement is also evident under a higher wavelength in this last absorption band; (C=N): 1512 cm$^{-1}$ and 1673 cm$^{-1}$, with the latter having a large intensity. For (N—H) and (O—H): 3406 cm$^{-1}$, a large and intense bandwidth is observed due to the overlapping of the respective bands of each functional group since the reaction environment of the compound (b) was methanol. Additionally, no bands were detected for the functional group (C—H), whose absorption range is 2960-2850 cm$^{-1}$, since the bands can also be overlapped with the large band (N—H) and (O—H), as a consequence of their size and absorption intensity.

Figure 8:
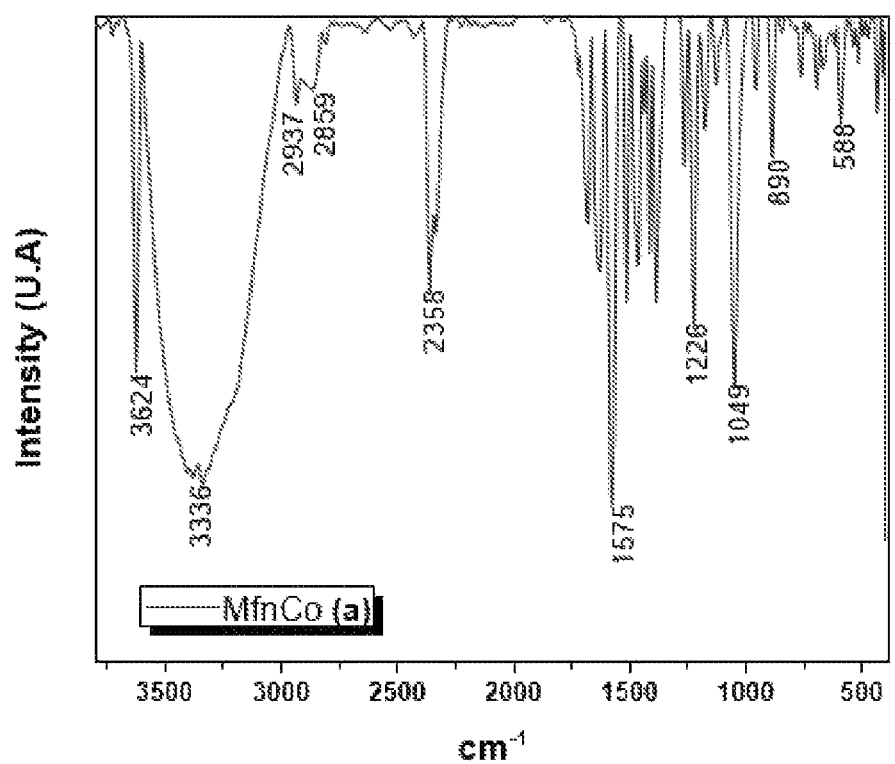
FIG. 8. Illustrates the Fourier transform infrared (FTIR) spectroscopic chart of the coordination compound of cobalt (II) with method 1 (*a*).

FIG. 8 shows the infrared spectrum for the copper coordination compound. The characteristic bands of the functional groups can be seen: (C—N): 1278 cm$^{-1}$; (C=N): 1676 cm$^{-1}$; (C—H): 3164 cm$^{-1}$ and (N—H): 3216 cm$^{-1}$, 3358 cm$^{-1}$ and 3398 cm$^{-1}$.

Figure 9:
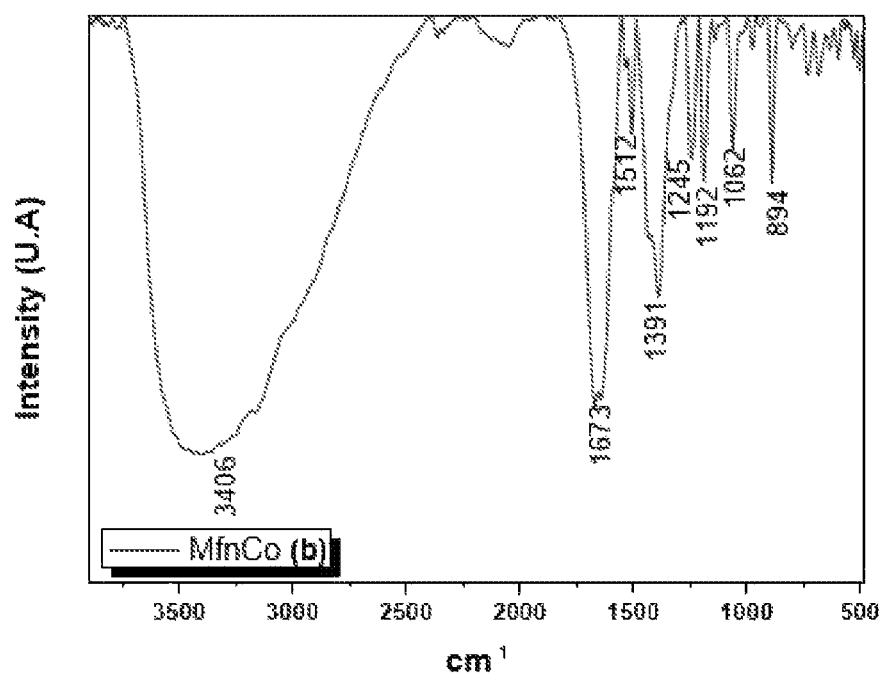
FIG. 9. Illustrates the Fourier transform infrared (FTIR) spectroscopic chart of the coordination compound of cobalt (II) with method 2 (*b*).

FIG. 9 shows the infrared spectrum for the copper (II) coordination compound method 1 (d); the characteristic bands of the functional groups are seen: (C—N): 1266 cm$^{-1}$; (C=N): 1519 cm$^{-1}$ y 1645 cm$^{-1}$; (C—H): 3254 cm$^{-1}$ and for (N—H): a 3372 cm$^{-1}$ and 3431 cm$^{-1}$.

Figure 10:
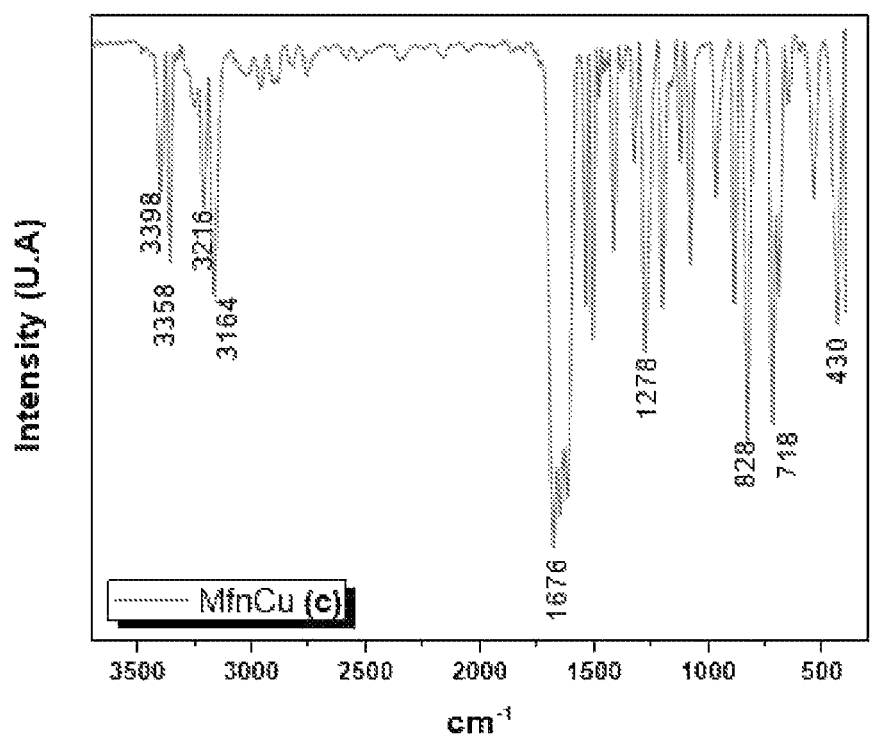
FIG. 10. Illustrates the Fourier transform infrared (FTIR) spectroscopic chart of the coordination compound of copper (II) with method 1 (*c*).

FIG. 10 shows the spectrum obtained for the copper (II) coordination compound through method 2 (e). The characteristic bands for the functional groups were: (C—N): 1058 cm$^{-1}$ and 1277 cm$^{-1}$; (C=N): 1567 cm$^{-1}$ and 1621 cm$^{-1}$; (C—H): 2851 and 2941 cm$^{-1}$; (N—H) a 3285 cm$^{-1}$; 3381 cm$^{-1}$ and 3464 cm$^{-1}$. An intense band is observed at 2335 cm$^{-1}$ that is caused by the presence of $CO_2$ when samples are measured.

Figure 11:
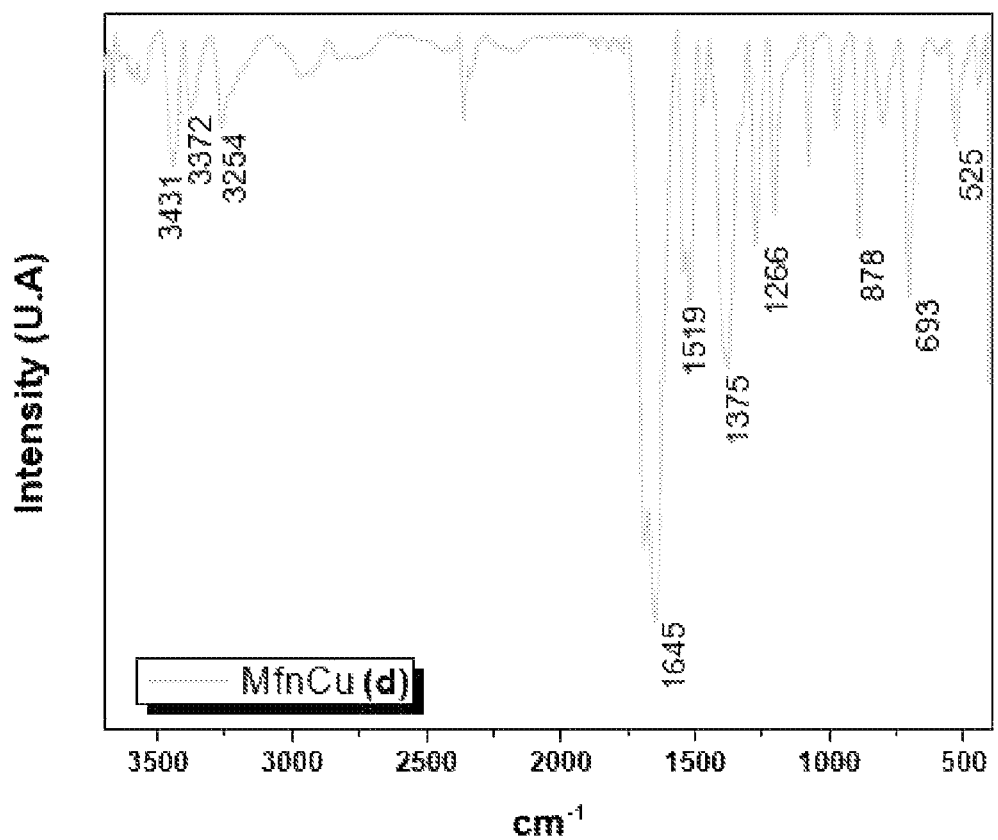
FIG. 11. Illustrates the Fourier transform infrared (FTIR) spectroscopic chart of the coordination compound of copper (II) with method 1 (*d*).

FIG. 11 corresponds to the infrared spectrum of the nickel (II) coordination compound method 1 (f). The characteristic bands of the functional groups are: (C—N): 1041 cm$^{-1}$ and 1372 cm$^{-1}$ for the complex, showing a displacement in higher wavelengths in this last band; (C=N): 1572 cm$^{-1}$; (C—H): 2801 cm$^{-1}$ and (N—H): 3227 cm$^{-1}$, 3344 cm$^{-1}$ and 3458 cm$^{-1}$.

Figure 12:
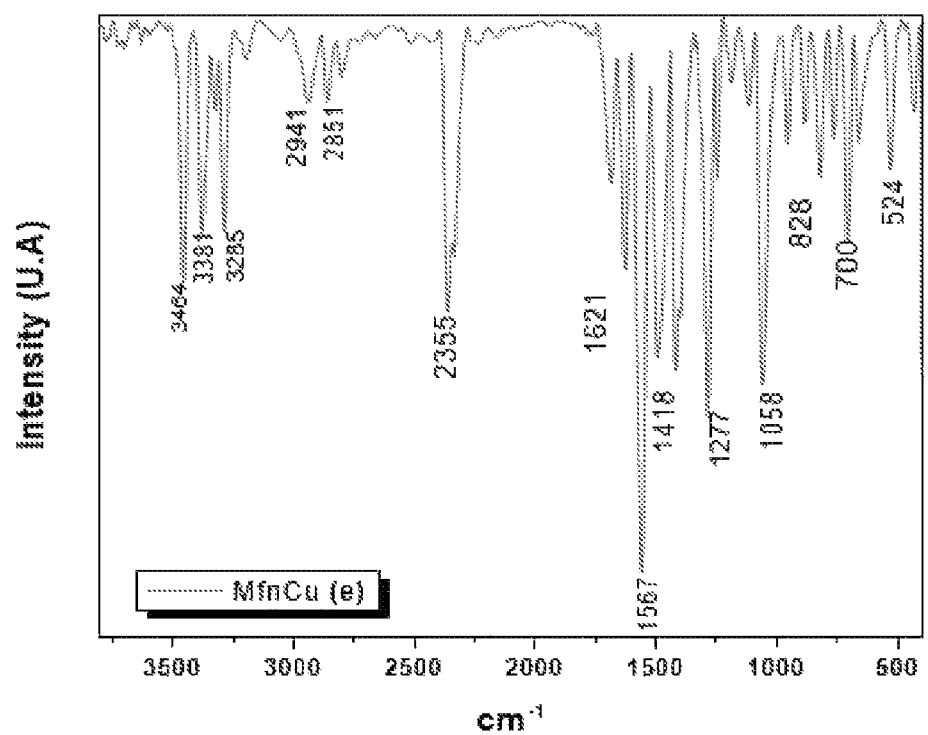
FIG. 12. Illustrates the Fourier transform infrared (FTIR) spectroscopic chart of the coordination compound of copper (II) with method 2 (*e*).

FIG. 12 corresponds to the infrared spectrum of the nickel (II) coordination compound method 2 (g). The characteristic bands of the functional groups are: (C—N): 1058 cm$^{-1}$ and 1306 cm$^{-1}$; (C=N): 1572 cm$^{-1}$. A strong band is present at 1469 cm$^{-1}$, which corresponds to the two methyl radical groups combined with the tertiary amine. For (C—H): 2803, 2864, 2936 and 3001 cm$^{-1}$; (N—H): 3248, 3342 cm$^{-1}$ 3431 and 3496 cm$^{-1}$.

Figure 13:
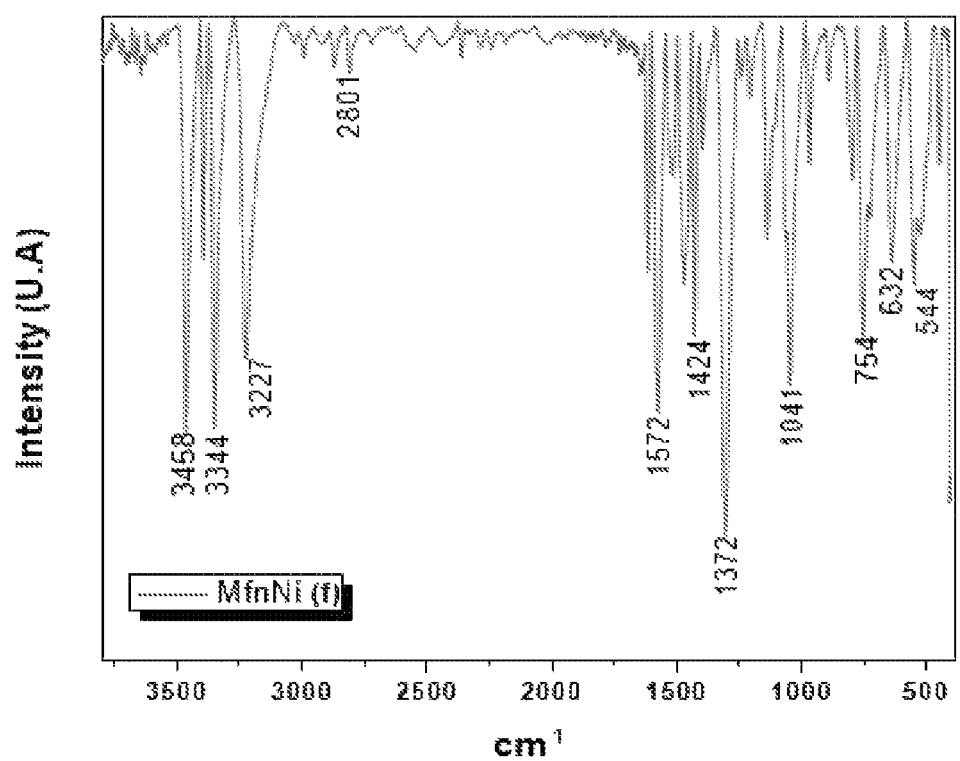
FIG. 13. Illustrates the Fourier transform infrared (FTIR) spectroscopic chart of the coordination compound of copper (II) with method 1 (*f*).

FIG. 13 corresponds to the infrared spectrum of the zinc (II) coordination compound (h). The characteristic bands of the functional groups are: (C—N): 1076 cm$^{-1}$, 1180 cm$^{-1}$ and 1240 cm$^{-1}$, with a slight displacement under higher wavelengths in this last absorption band; (C=N): 1666 cm$^{-1}$, which is the highest absorption in the entire spectrum. A band is also detected at 1491 cm$^{-1}$ which corresponds to two radical metal groups combined with the tertiary amine. (C—H): 2831 cm$^{-1}$, and 2940 cm$^{-1}$ and (N—H): 3272 cm$^{-1}$, 3350 cm$^{-1}$ and 3437 cm$^{-1}$.

Figure 14:
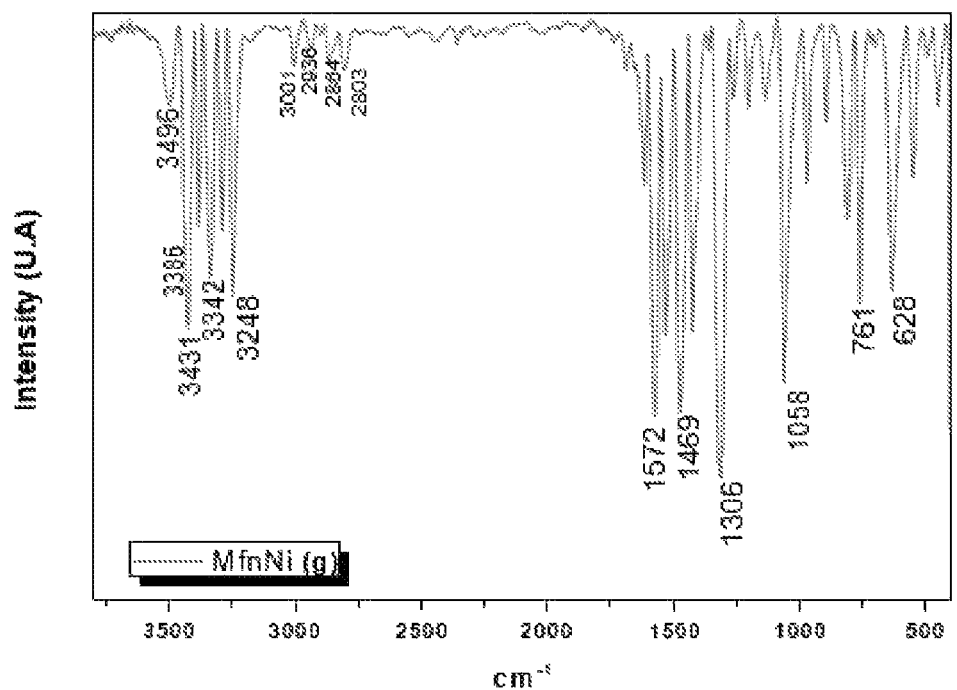
FIG. 14. Illustrates the Fourier transform infrared (FTIR) spectroscopic chart of the coordination compound of nickel (II) with method 2 (*g*).
Figure 15:
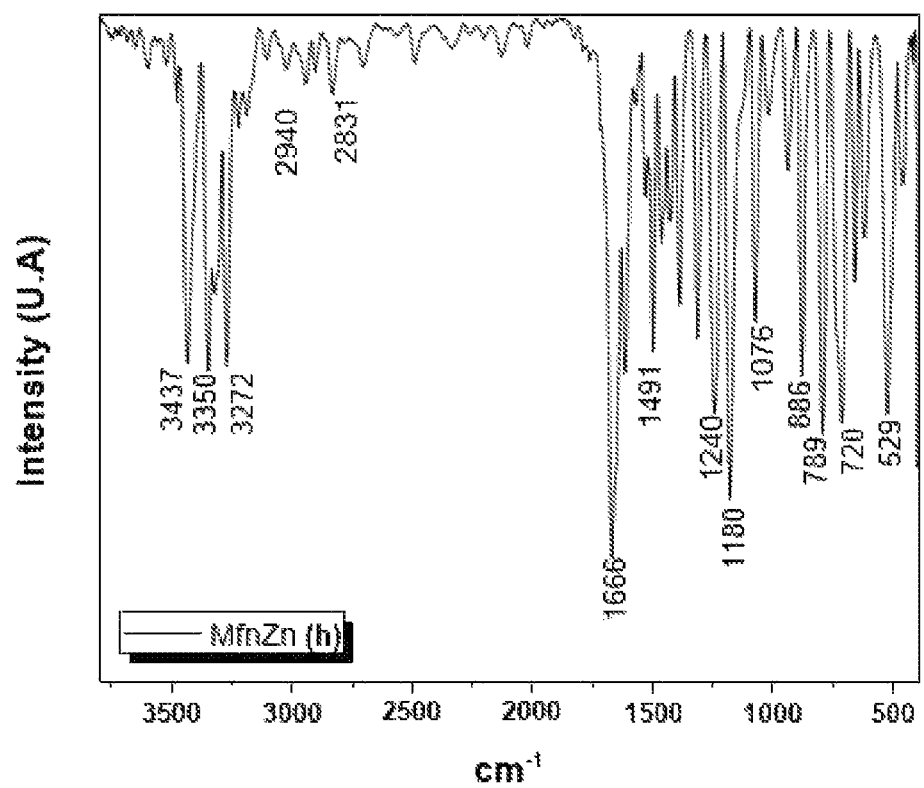
FIG. 15. Illustrates the Fourier transform infrared (FTIR) spectroscopic chart of the coordination compound of zinc (II) (h).

FIG. 14 corresponds to the infrared spectrum of the bismuth (III) coordination compound. The characteristic bands of the functional groups are: (C—N): 1058 cm$^{-1}$ and 1377 cm$^{-1}$, with a slight displacement under higher wavelengths in this last absorption band; (C=N): 1585 y 1628 cm$^{-1}$; (C—H): 2948 cm$^{-1}$ and finally (N—H): 3172 cm$^{-1}$ and 3365 cm$^{-1}$.

Table 3 shows a summary of the absorption values for each compound.

Figure 16:
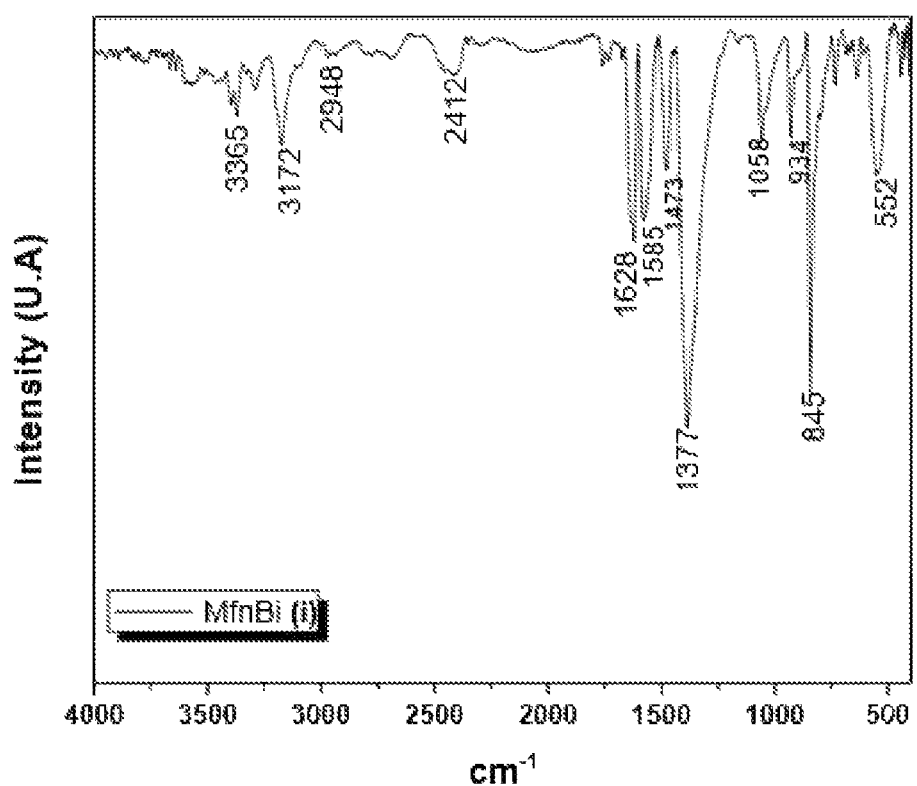
FIG. 16. Illustrates the Fourier transform infrared (FTIR) spectroscopic chart of the coordination compound of bismuth (III) (i).

The thermogravimetric analysis (TGA) and differential scanning calorimetry (DSC), delivered the following results:

FIG. 16 shows the thermogravimetric analysis (TGA) and differential scanning calorimetry (DSC) for the cobalt (II) metformin complex with method 1 (a). Two losses of mass can be evidenced. They are marked in the TGA curve as 1 and 2, with the mass loss percentages presented in Table 4. It is noteworthy to mention that possible molecular structures can be proposed that match the mass of the compound.

TABLE 3

Absorptions in the IR spectrum of the obtained coordination compounds.

| Compound | functional Group | Vibration (cm$^{-1}$) |
|---|---|---|
| Metformin | C—N | 1053, 1163 |
|  | C=N | 1562, 1629 |
|  | C—H | 2811 |
|  | N—H | 3168, 3293, 3377 |
| MfnCo (a) | C—N | 1049, 1226 |
|  | C=N | 1575 |
|  | C—H | 2859, 2937 |
|  | N—H | 3336, 3624 |
| MfnCo (b) | C—N | 1062, 1192, 1245 |
|  | C=N | 1512, 1673 |
|  | C—H |  |
|  | N—H | 3406 |
| MfnCu (c) | C—N | 1278 |
|  | C=N | 1676 |
|  | C—H | 3164 |
|  | N—H | 3216, 3358, 3398 |
| MfnCu (d) | C—N | 1266 |
|  | C=N | 1519, 1645 |
|  | C—H | 3254 |
|  | N—H | 3372, 3431 |
| MfnCu (e) | C—N | 1058, 1277 |
|  | C=N | 1567, 1621 |
|  | C—H | 2851, 2941 |
|  | N—H | 3285, 3381, 3464 |
| MfnNi (f) | C—N | 1041, 1372 |
|  | C=N | 1572 |
|  | C—H | 2801 |
|  | N—H | 3227, 3344, 3458 |
| MfnNi (g) | C—N | 1058, 1306 1572 |
|  | C=N | 2803, 2864, 3001 |
|  | C—H | 3248, 3342, 3431, 3496 |
|  | N—H |  |
| MfnZn (h) | C—N | 1076, 1180, 1240 1666 |
|  | C=N | 2831, 2940 |
|  | C—H | 3272, 3350, 3437 |
|  | N—H |  |
| MfnBi (i) | C—N | 1058, 1377 |
|  | C=N | 1585, 1628 |
|  | C—H | 2948 |
|  | N—H | 3172, 3365. |

For this compound, the molecular formula [Co(C$_4$H$_{11}$N$_5$)](Cl)$_2$·1/2H$_2$O is proposed, and, according to the calculations, the theoretical mass loss percentages corresponding to the experimental mass losses (marked as 1 and 2 in the TGA curve) are related with the loss of % of the water molecule and the loss of the ligand molecule, respectively.

Figure 17:
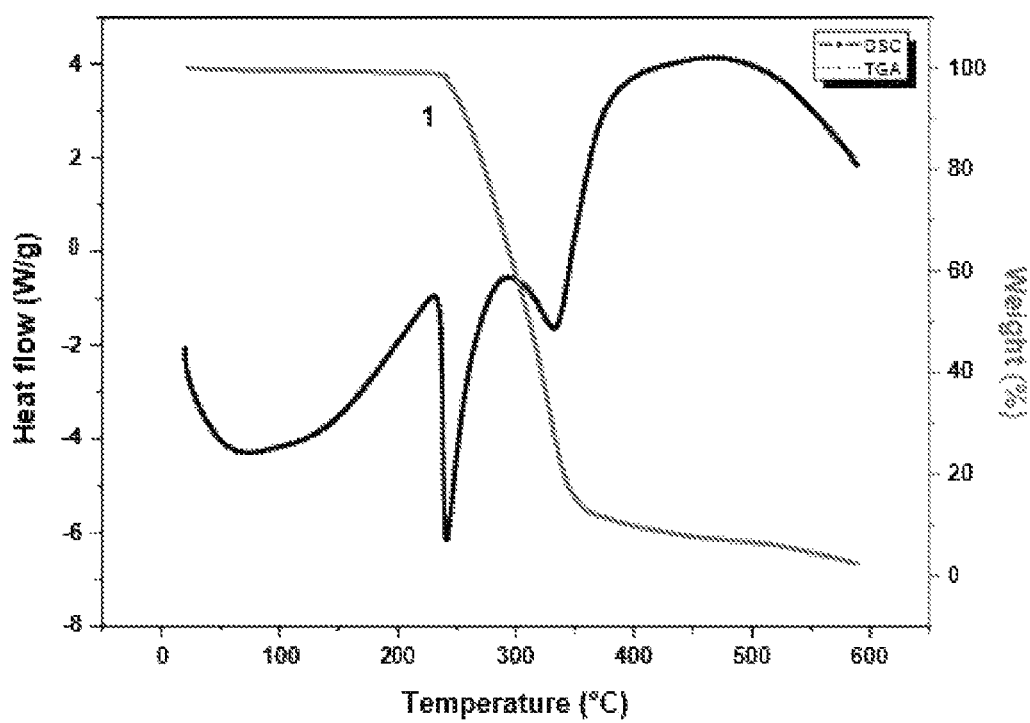
FIG. 17. Illustrates the thermogravimetric analysis (TGA) chart and the differential scanning calorimetry (DSC) for the hydrochloride metformin ligand.

FIG. 17 corresponds to the thermogravimetric analysis (TGA) and differential scanning calorimetry (DSC) for the cobalt (II) metformin complex with method 2, where two mass losses can be observed, marked as 1 and 2 in the TGA curve, whose experimental mass loss percentages are presented in Table 4.

For this compound, the molecular formula is [Co(C$_4$H$_{11}$N$_5$)$_3$](Cl)$_2$·(H$_2$O)$_2$ according to the characterization by single crystal XRD, and hence, the calculation of the theoretical mass loss percentage was carried out (see Annexes). According to the calculations, the experimental mass losses, corresponding to the TGA curve (marked as 1 and 2), are tied to the loss of two crystallization water molecules and the loss of two ligand molecules.

Figure 18:
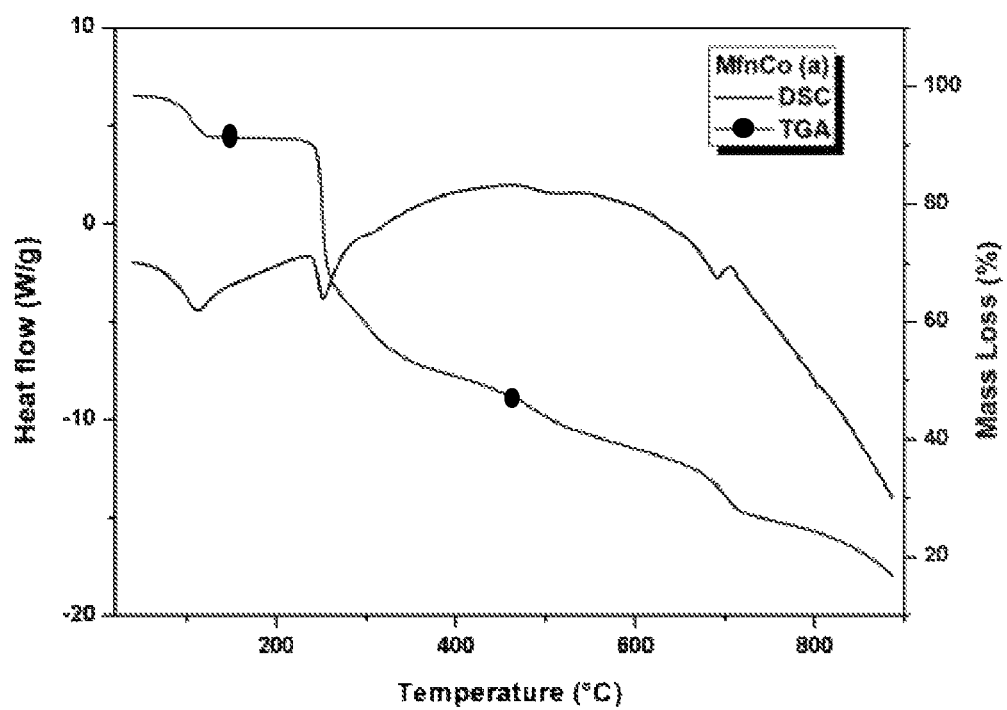
FIG. 18. Illustrates the thermogravimetric analysis (TGA) chart and the differential scanning calorimetry (DSC) for the metformin-cobalt (II) complex with method 1 (a).

FIG. 18 reveals the thermogravimetric analysis (TGA) and differential scanning calorimetry for the copper (II) metformin complex with method 1 (c), where two significantly different mass loss intervals are appreciated, marked as 1 and 2 in the curve, whose theoretical mass loss percentages are shown in Table 4.

For this compound, the proposed molecular formula is $[Cu(C_4H_{11}N_5)(Cl)_2]\cdot1/4H_2O$ and the calculation of the theoretical mass loss percentage was carried out (see Annexes). According to the calculations, the experimental mass losses, corresponding to the TGA curve marks 1 and 2, are caused by the loss of the water molecule and the ligand molecule, respectively.

Figure 19:
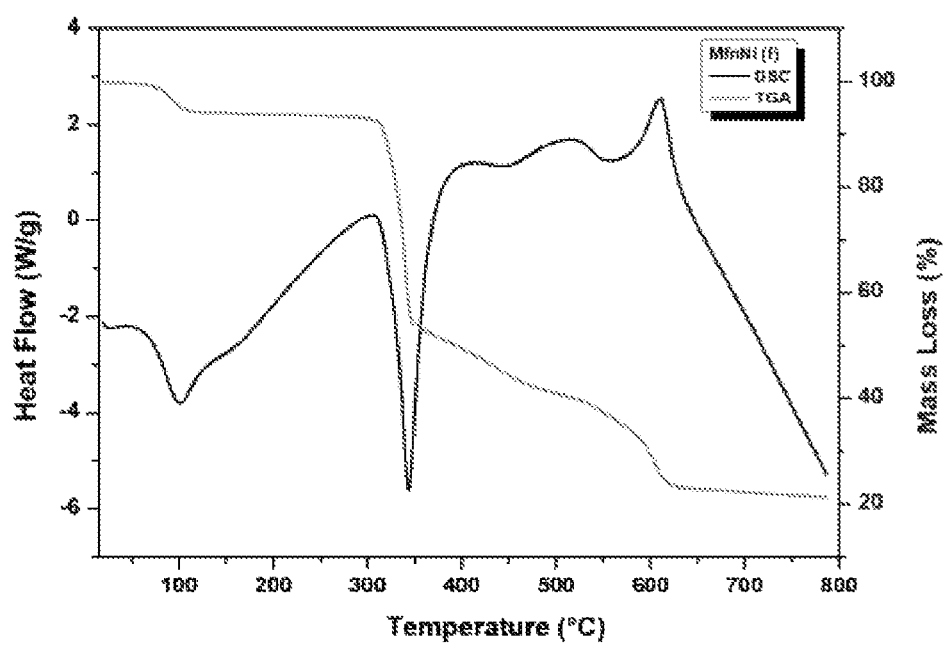
FIG. 19. Illustrates the thermogravimetric analysis (TGA) chart and the differential scanning calorimetry (DSC) for the metformin-nickel (II) complex with method 1 (c).

FIG. 19 shows the thermogravimetric analysis (TGA) and differential scanning calorimetry (DSC) for the copper (II) metformin complex with method 1 (d). The compound (d) was obtained from the same reaction environment than the compound (c); However, when calculating the mass loss percentages, it was determined that the proposed molecular formulas for both compounds do not match. Hence, the molecular formula $[Cu(C_4H_{11}N_5)(Cl)_2]\cdot2H_2O$ is proposed for compound (d).

The thermogram shows two significantly different mass losses, signaled as 1 and 2 in the TGA curve, whose experimental mass loss percentages are shown in Table 4. According to the proposed molecular formula, the corresponding calculations were carried out (see Annexes). Hence, the experimental mass losses marked as 1 and 2 are related to the loss of water molecules of the compound, followed by the loss of the ligand molecule.

Figure 20:
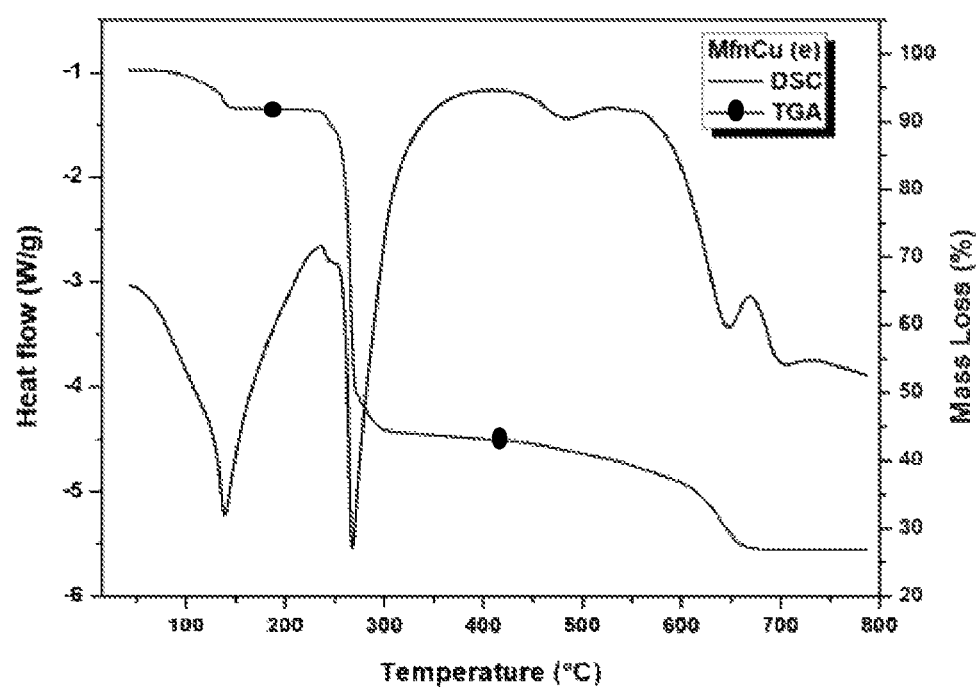
FIG. 20. Illustrates the thermogravimetric analysis (TGA) chart and the differential scanning calorimetry (DSC) for the metformin-copper (II) complex with method 1 (f).

FIG. 20 shows the thermogravimetric analysis (TGA) and differential scanning calorimetry (DSC) for the copper (II) metformin complex with method 2 (e), where three significantly different masses are evidenced and marked as 1, 2 and 3, whose experimental mass loss percentages are shown in Table 4.

For this compound, the molecular formula $[Cu(C_4H_{11}N_5)(Cl)_2]\cdot H_2O$ is proposed, and the theoretical mass loss percentage was calculated (see Annexes). According to calculations, the experimental mass losses marked as 1, 2 and 3, are caused by the loss of the water molecule present in its formula, loss of the ligand and elimination of the two Cl molecules, respectively.

Figure 21:
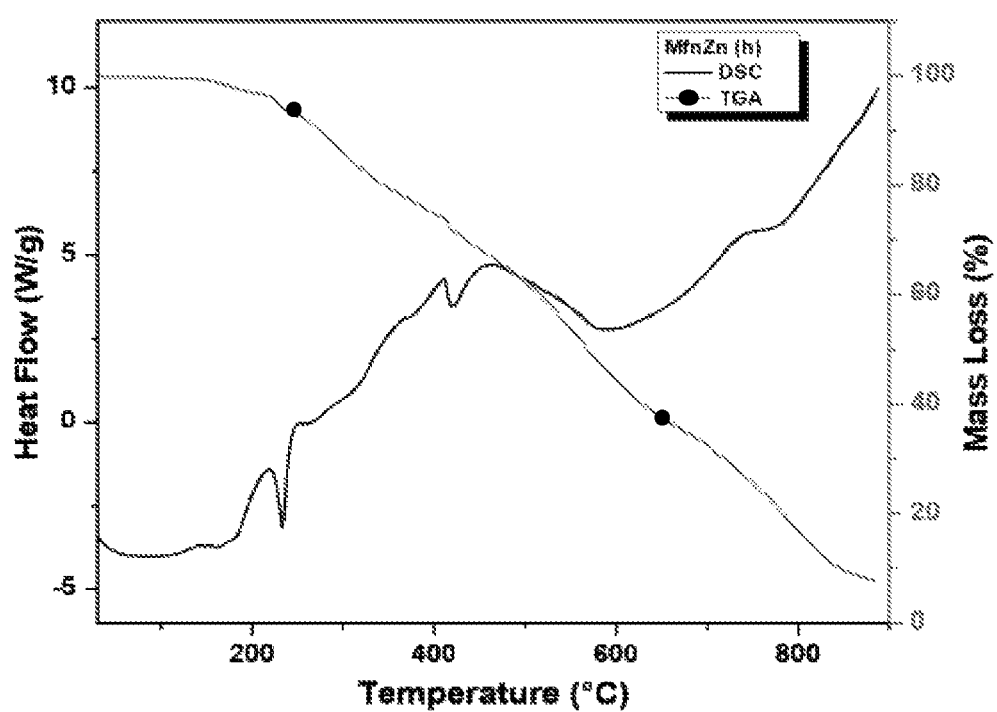
FIG. 21. Illustrates the thermogravimetric analysis (TGA) chart and the differential scanning calorimetry (DSC) for the metformin-zinc (II) (h).

FIG. 21 corresponds to the thermogravimetric analysis (TGA) and differential scanning calorimetry (DSC) for the nickel (II) metformin complex method 1 (f). The thermogravimetric analysis was carried out, thus revealing two significantly different mass losses (marked as 1 and 2) whose experimental mass loss percentage is presented in Table 4.

For this compound, the following molecular formula was proposed: $[Ni(C_4H_{11}N_5)(C_4H_{10}N_5)]Cl$. The theoretical mass percentage was calculated, and accordingly, it was determined that the mass losses correspond to the initial loss of a ligand molecule, followed by the loss of a second ligand molecule.

Figure 22:
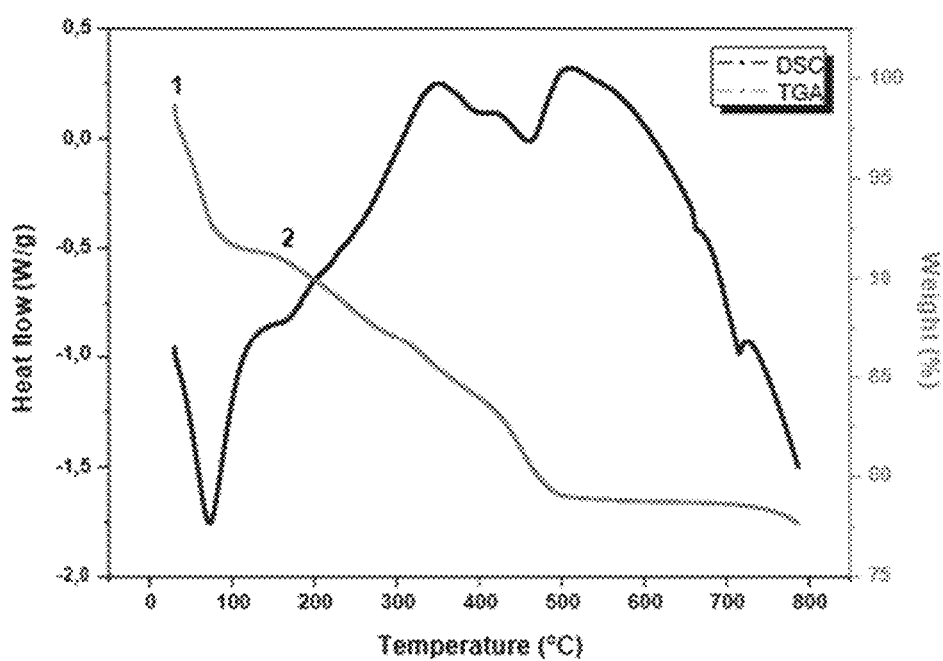
FIG. 22. Illustrates the thermogravimetric analysis (TGA) chart and the differential scanning calorimetry (DSC) for the metformin-bismuth (III) (i).

FIG. 22 illustrates the thermogravimetric analysis (TGA) and differential scanning calorimetry (DSC) for the nickel (II) metformin complex with method 2, where two significantly different mass losses, marked in the TGA curve as 1 and 2, whose experimental mass loss percentages are shown in Table 4.

For this compound, it is assumed that the molecular formula is $[Ni(C_4H_{11}N_5)_2](Cl^-)(OH^-)$. However, it is noteworthy to mention that, although the same molecular formula is assumed, there are different phases according to the XRD powder analysis. Hence, the theoretical mass loss percentages (see Annexes) were computed which led to state that the first mass loss is caused by the loss of a ligand molecule and the OH⁻ anion, while the second loss corresponds to the ligand molecule.

Figure 23:
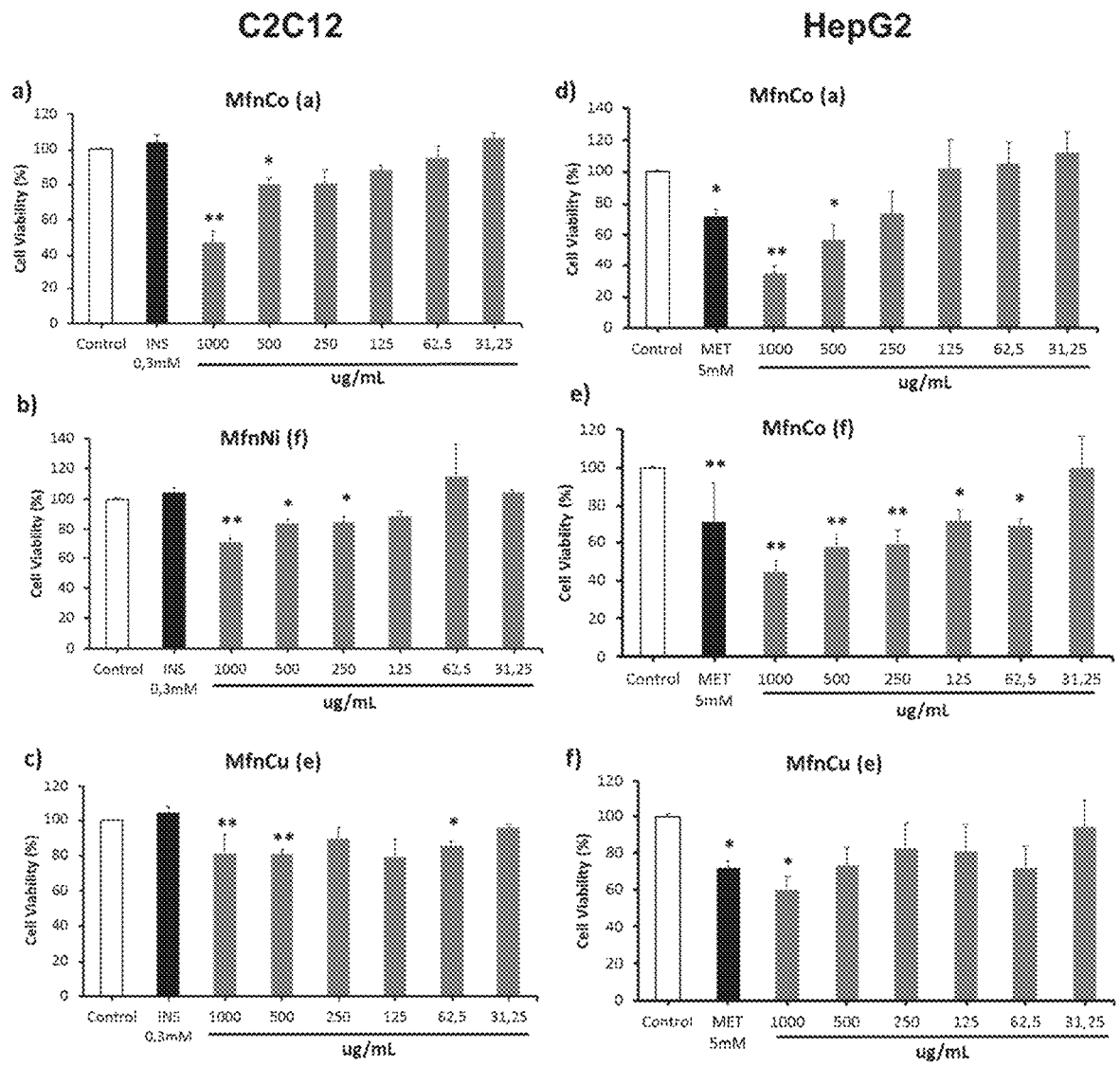
FIG. 23. Illustrates the cytotoxicity of different molecules on cell lines C2C12 and HepG2.

FIG. 23 shows the thermogravimetric analysis (TGA) and differential scanning calorimetry (DSC) for the zinc (II) metformin complex (h), where a single mass loss is evidenced and marked in the TGA curve as 1 (see FIG. 36), whose experimental mass loss percentage is shown in Table 4.

For this compound, the molecular formula $[Zn(C_4H_{11}N_5)Cl_3]$ was proposed, and the theoretical mass loss was calculated accordingly. The mass loss corresponds to the total decomposition of the molecule.

FIG. 24 corresponds to the thermogravimetric analysis (TGA) and differential scanning calorimetry (DSC) for the bismuth (III) (i) metformin complex. It shows two mass losses marked as 1 and 2 in the TGA curve, whose experimental mass loss percentages are presented in Table 4. Furthermore, the TGA curve shows that the decomposition is incomplete since the decline of the curve reaches the 75-80% interval, where it remains constant until the experiment is concluded.

For this compound, the molecular formula $[Bi(C_4H_{11}N_5)_3](NO_3)$ is proposed, and the theoretical mass loss was calculated accordingly. The mass losses correspond to the loss of the nitrate anion and the elimination of one ligand molecule.

TABLE 4

Theoretical and experimental mass loss percentages and proposed formula for the obtained coordination compounds obtained.

| Sample | % Theoretical mass loss | % Experimental mass loss | Proposed formula |
| --- | --- | --- | --- |
| Ligand |  | 95.4% | $(C_4H_{12}N_5)Cl$ |
| MfnCo (a) | 3.3% | 3.2% | $[Co(C_4H_{11}N_5)](Cl)_2\cdot\frac{1}{2}H_2O$ |
|  | 48.1% | 46.05% |  |
| MfnCo (b) | 6.51% | 6.87% | $[Co(C_4H_{11}N_5)_3](Cl)_2\cdot(H_2O)_2$ |
|  | 46.68% | 49.74% |  |
| MfnCu (c) | 1.67% | 1.5% | $[Cu(C_4H_{11}N_5)Cl_2]\cdot_{1/4}H_2O$ |
|  | 48.17% | 49.46% |  |
| MfnCu (d) | 12.01% | 13.63% | $[Cu(C_4H_{11}N_5)Cl_2]\cdot2H_2O$ |
|  | 43.11% | 41.77% |  |
| MfnCu (e) | 8.4% | 8.1% | $[Cu(C_4H_{11}N_5)_2](Cl)_2\cdot H_2O$ |
|  | 60.2% | 64.3% |  |
| MfnNi (f) | 4.9% | 5.8% | $[Ni(C_4H_{11}N_5)(C_4H_{10}N_5)]Cl\cdot H_2O$ |
|  | 69.6% | 73.2% |  |
| MfnNi (g) | 39.5% | 35.199% | $[Ni(C_4H_{11}N_5)_2](Cl)(OH)$ |
|  | 34.96% | 32.827% |  |
| MfnZn (h) | 82.03% | 86.65% | $[Zn(C_4H_{11}N_5)(Cl)_3]$ |
| MfnBi (i) | 9.41% | 7.14% | $[Bi(C_4H_{11}N_5)_3](NO_3)$ |
|  | 19.6% | 14.5% |  |

The obtained metformin-metal complexes of Co(II), Ni(II) and Cu(II) were cell viability evaluated in C2C12 (ATCCCRL-1772TM) mouse muscle cells and HepG2 (ATCC HB-8065TM) human liver carcinoma cells by the MTT assay after the treatment of the three different compounds for 4 hours (C2C12) or 48 hours (HepG2), to determine the potential of the compounds as new safe drugs. The results demonstrate that the compounds exhibit low cytotoxicity at doses less than 250 µg/ml with a cell viability greater than 80%.

Cell viability was evaluated using the MTT assay, as is showed in FIG. 25.

FIG. 25 shows the cytotoxicity of different molecules on cell lines C2C12 and HepG2. Cells seeded in 96-well plates were treated with the molecules for 4 h (C2C12) or 48H (HepG2). The cytotoxicity was evaluated by MTT assay. Values are expressed as mean±SEM. ANOVA with post-hoc Tukey for multiple comparisons was performed. **: $p<0.01$; *: $p<0.05$. n=3. Insulin 0.3 mM (INS) and metformin 5 mM (MET) are used as positive control.

The invention claimed is:

1. A metformin-copper complex, wherein the metformin-copper complex is in a crystalline form characterized by a powder X-ray diffraction pattern comprising the following 2Θ values: 9.65; 11.78; 14.05; 15.31; 16.42; 18.79; 18.90; 19.37; 20.31; 21.40; 23.15; 23.49; 23.82; 24.33; 24.80; 24.92; 25.25; 26.03; 26.82; 28.22; 29.07; 29.22; 30.33; 30.68; 31.48; 31.81; 32.00; 32.08; 33.02; 33.19; 33.61; 33.94; 34.59; 35.73; 36.04; 36.42; 36.72; 36.89; 37.07; 37.95; 38.21; 38.33; 38.58; 38.91; 39.19; 39.39; 40.54; 40.64; 40.80; 40.95; 41.30; 41.57; 41.79; 42.39; 42.86; 43.05; 43.23; 43.41; 43.59; 44.10; 44.23; 44.78; 45.10; 45.27; 45.86; 46.07; 46.94; 47.14; 47.33; 47.54; 48.02; 48.20; 48.45; 48.63; 48.84; 49.12; 49.52; and 49.72.

2. A pharmaceutical composition comprising the metformin-copper complex of claim 1.

3. A method of treating a disease in a patient in need thereof, the method comprising administering to the patient a therapeutically effective dose of the metformin-copper complex of claim 1.

4. The method of claim 3, wherein the disease is diabetes, obesity, hypertriglyceridemia, hyperglycemia, atherosclerosis, cancer or combinations thereof.

* * * * *